(12) United States Patent
Hitchcock et al.

(10) Patent No.: US 10,068,757 B2
(45) Date of Patent: Sep. 4, 2018

(54) STRONG FIELD PHOTOIONIZATION ION SOURCE FOR A MASS SPECTROMETER

(71) Applicant: Thermo Finnigan LLC, San Jose, CA (US)

(72) Inventors: James M. Hitchcock, Pflugerville, TX (US); Scott T. Quarmby, Round Rock, TX (US)

(73) Assignee: Thermo Finnigan LLC, San Jose, CA (US)

( * ) Notice: Subject to any disclaimer, the term of this patent is extended or adjusted under 35 U.S.C. 154(b) by 93 days.

(21) Appl. No.: 14/942,743

(22) Filed: Nov. 16, 2015

(65) Prior Publication Data

US 2017/0140913 A1 May 18, 2017

(51) Int. Cl.
*H01J 49/04* (2006.01)
*H01J 49/16* (2006.01)
*G01N 30/72* (2006.01)

(52) U.S. Cl.
CPC ........ *H01J 49/162* (2013.01); *G01N 30/7206* (2013.01); *H01J 49/161* (2013.01)

(58) Field of Classification Search
CPC ........................... H01J 49/162; G01N 30/7206
See application file for complete search history.

(56) References Cited

U.S. PATENT DOCUMENTS

| | | | | |
|---|---|---|---|---|
| 3,478,204 A * | 11/1969 | Brubaker | ............... | H01J 49/161 |
| | | | | 250/423 P |
| 5,117,108 A * | 5/1992 | Muller | ................. | H01J 49/164 |
| | | | | 250/288 |
| 5,629,518 A * | 5/1997 | Grotheer | ............. | H01J 49/0422 |
| | | | | 250/287 |
| 5,955,731 A * | 9/1999 | Bergmann | .......... | H01J 49/0463 |
| | | | | 250/288 |
| 6,707,039 B1 * | 3/2004 | Truche | .................. | H01J 49/164 |
| | | | | 250/282 |
| 7,064,317 B2 | 6/2006 | McLuckey et al. | | |
| 9,431,229 B2 * | 8/2016 | Yorisaki | ............. | H01J 49/0409 |
| 2003/0052268 A1 | 3/2003 | Doroshenko et al. | | |

(Continued)

FOREIGN PATENT DOCUMENTS

WO    WO 2013/098610 A1    7/2013

OTHER PUBLICATIONS

DeWitt et al., "Near-infrared femtosecond photoionization/dissociation of cyclic aromatic hydrocarbons", J. Chem. Phys., vol. 102 (21), 1995, pp. 8670-8673.

(Continued)

*Primary Examiner* — Brooke Purinton
(74) *Attorney, Agent, or Firm* — Thomas F. Cooney

(57) ABSTRACT

An ion source for a mass spectrometer comprises: an evacuated chamber having an interior receiving a gaseous sample effluent stream; a source of light pulses of pulse width 150 femtoseconds or less; a window of the evacuated chamber through which the light pulses pass into the evacuated chamber interior; one or more mirrors within the evacuated chamber disposed such that the light pulses are reflected from each of the one or mirrors such that the reflected pulses are caused to focus at one or more focal regions within the effluent stream within the evacuated chamber interior; and a pair of electrodes disposed at opposite sides of the one or more focal regions.

9 Claims, 17 Drawing Sheets

(56) References Cited

U.S. PATENT DOCUMENTS

| | | | | |
|---|---|---|---|---|
| 2004/0245453 A1* | 12/2004 | Izgarian | ............... | H01J 49/063 250/288 |
| 2005/0056776 A1* | 3/2005 | Willoughby | ............ | H01J 49/06 250/288 |
| 2007/0295902 A1* | 12/2007 | Shea | ................... | H01J 49/0454 250/288 |
| 2009/0039282 A1* | 2/2009 | Haase | ................... | H01J 49/164 250/423 R |
| 2010/0243882 A1* | 9/2010 | Loyd | ................ | G02B 27/0006 250/282 |
| 2013/0099112 A1* | 4/2013 | Haase | ................... | H01J 49/164 250/282 |
| 2014/0175276 A1* | 6/2014 | Giuliani | ............. | H01J 49/0031 250/282 |
| 2014/0224974 A1* | 8/2014 | Kenny | ............... | H01J 49/0059 250/282 |
| 2015/0008313 A1* | 1/2015 | Loboda | ................ | H01J 49/164 250/282 |
| 2015/0185190 A1* | 7/2015 | Zhang | .................... | G01N 27/64 250/288 |
| 2017/0140913 A1* | 5/2017 | Hitchcock | ............. | H01J 49/162 |

OTHER PUBLICATIONS

Peng et al., "High-Pressure Gas Phase Femtosecond Laser Ionization Mass Spectrometry", Anal. Chem. 2012, 84, pp. 5633-5640.

\* cited by examiner

STRONG FIELD PHOTOIONIZATION ION SOURCE FOR A MASS SPECTROMETER

FIELD OF THE INVENTION

The present invention relates generally to mass spectrometry, and more particularly to ion sources utilized to produce ions in mass spectrometers.

BACKGROUND OF THE INVENTION

Mass spectrometry is widely used in analytical chemistry and other fields for identifying unknown compounds, screening for the presence of certain target compounds, identifying the products of chemical reactions, studying the kinetics or mechanisms of chemical reactions, etc. Since mass spectrometers are capable of directly detecting only ions, provision must be made for ionizing the molecular constituents of samples to be analyzed. Many different types of ion sources are available for this purpose.

In electron ionization (EI) ion sources, the electrons emitted from a thermionic filament are caused to directly impinge upon gaseous molecules of one or more chemical constituents of a sample under investigation. These chemical constituents may include one or more analyte compounds or matrix compounds derived from the sample. The interaction of energetic electrons of the electron beam with an electron cloud of a neutral molecule may effectively "dislodge" one or more electrons of the neutral molecule and may additionally cleave chemical bonds. This combination of ionization and fragmentation may lead to the formation of one or more cation species. These cation species are analyzed by a mass analyzer. Such electron ionization sources are commonly employed in gas chromatography/mass spectrometry (GCMS) instruments.

FIG. 1 is a symbolic diagram of an ion source 1 configured to produce analyte ions by electron ionization (EI). Ion source 1 includes an ionization volume 2 into which sample molecules including analyte molecules are introduced via, for example, an end portion of a gas chromatograph (GC) column 3. The GC column 3 may be a fused silica capillary tube of a type well known in the art. Ionization volume 2 is located inside a vacuum chamber evacuated to a suitable pressure by a not-illustrated pumping system. A stream of electrons is generated by passing an electric current provided by a filament electric current source 9 through thermionic filament 4. The filament current source 9 is located externally to the vacuum chamber and electrically connected to the filament 4 via a vacuum feed-through (not shown). Filament 4 is typically fabricated from a refractory metal such as rhenium (or alloys thereof). The refractory metal may include a low work function coating such as thorium oxide or yttrium oxide. Electrons emitted by filament 4 travel, under the influence of an electrical field established by applying suitable potentials to the filament 4 and electrodes 6, through aperture 5 into the ionization volume 2 interior. The electron beam may also be guided by a magnetic field established by magnets (not shown) located behind and on the opposite side of ionization volume 2 from filament 4. The electrons interact with the sample molecules within ionization volume 2 to form sample ions. The sample ions are extracted from ionization volume 2 via ion exit aperture 7 by ion lenses 8, and are transported through an ion guide or other suitable ion optics to a mass analyzer for analysis.

Unfortunately, the ionization efficiency of EI is restricted to a maximum of about 0.01% due to the electron beam current density being limited by space charge. If the electrons are given a kinetic energy in the range of 50-100 eV, the de Broglie wavelength of the electron is about the same as a chemical bond length and energy transfer is maximized. Greater electron energy does not improve efficiency. If the imparted kinetic energy is greater than 100 eV, then the de Broglie wavelength is smaller than bond lengths and the molecules become transparent to the electrons. Electron ionization is often considered to be a "hard" ionization technique, causing extensive ion fragmentation. This property is detrimental for use of EI in conjunction with analyses that make use of selected-reaction-monitoring (for example, analyses of proteins and other biological molecules) in which accurate analysis depends on experimental control of the degree of ion fragmentation.

In contrast to EI, photoionization techniques are often considered to be "soft" ionization techniques, generating a higher proportion of molecular ions or ions formed by protonation of a molecule and creating fewer fragment ions than the EI technique. For example, the technique of single-photon ionization makes use of absorption, by each molecule, of an individual photon comprising sufficient energy to expel a valence electron from the molecule. Because it is mechanistically the simplest of the photoionization techniques, single-photon ionization is extensively employed in most conventional Atmospheric Pressure Photo-Ionization (APPI) ion sources. Typical ionization energies are such that either ultraviolet (UV) radiation sources emitting in the 150-320 nm range or vacuum-ultraviolet (VUV) radiation sources that emit wavelengths of 150 nm and shorter are generally required. Typical APPI ion sources may comprise a UV-emitting lamp or a VUV-emitting laser, such as an excimer laser, that illuminates a vaporized sample (e.g. an effluent from a gas chromatograph or a gas produced by evaporation of a liquid sample) with UV or VUV light. Although single-photon ionization is used extensively in APPI ion sources in the mass spectrometric study of a variety of analytes, it has some disadvantages as a general mass spectrometric ionization technique. Foremost among these is that the collision between a photon and an individual molecule is a statistically improbable process. Secondly, UV wavelengths and the shorter VUV wavelengths are strongly absorbed by common optical materials. For example, the optical transmission curves of borosilicate and soda-lime glasses decrease rapidly at wavelengths shorter than about 400 nm and even that of "UV glass" decreases rapidly at wavelengths shorter than about 250 nm—as well as by gaseous nitrogen. These difficulties can be overcome, in part, by proper choice of optical materials, by ionization in high vacuum and by providing high-photon-flux emitters. Nonetheless, present limitations cause the ionization efficiency of APPI to be significantly less than that of EI.

Multi-photon ionization techniques make use of the near-simultaneous absorption of more than one photon by an individual molecule, such that the combined absorbed energies exceed the ionization potential of the molecule. In such techniques, which include Resonance-Enhanced Multiphoton Ionization (REMPI), a first photon absorption event creates an electronically excited intermediate state. This is then followed, prior to the decay of the excited state, by another photon absorption event that causes ionization of the molecule. Because the near simultaneous absorption of two photons by a molecule is even more improbable than the absorption of a single photon, a very high photon flux is required.

Strong field photo-ionization (SFPI) is another photoionization technique that utilizes the electric field generated by an intense laser pulse to remove electrons from the gas chromatograph (GC) column effluent. The SFPI approach is both "softer" than traditional electron ionization (EI), thereby resulting in increased molecular ion formation, as well as more efficient than EI and single-photon and multi-photon techniques. Specifically, the SFPI method has been demonstrated to produce 100% ionization efficiency, at sufficient laser powers, for molecules inside the laser pulse's electric field as compared to, at best, 0.01% efficiency for electron ionization and presently-best-achievable 0.1% efficiency for single-photon absorption. Moreover, UV wavelengths are not required for SFPI, since absorption of photons by molecules is not required. Instead, ionization is caused by a large spatial electric field gradient produced by the simultaneous introduction of a large quantity of coherent photons. As a result, the SFPI technique can make use of pulsed light of any nominal emission wavelength.

The mechanism by which the SFPI technique generates ions is thought to be related to the mechanism of generation of UV light by High Harmonic Generation (HHG). The set of drawings shown in FIGS. 2A-2D illustrate the mechanism by which UV light is generated, according to the theory of HHG. The mechanistic steps illustrated in the first two drawings (FIGS. 2A-2B) are believed to also apply to ionization as observed in SFPI. FIG. 2A schematically shows the fundamental state of a valence electron 75$a$ (denoted e$^-$) of an atom in a gas in the absence of a perturbing electric field. In this drawing, curve 74$a$ schematically represents the potential energy of the electron versus distance away from the position of its valence shell. Residence within the valence shell represents a state of minimum potential energy for the valence electron. Horizontal line 72$a$ schematically represents the potential energy of the hypothetical free electron 75$b$, fully liberated from the atom. Thus, the vertical distance between the electron 75$a$ in the valence shell and the hypothetical free electron 75$b$ represents the normal ionization potential of the atom.

In the presence of a strong electrical field gradient (dE/dx) as produced by the passage of a high-energy laser pulse, both the electrical potential energy in free space 72$b$ and the potential energy associated with bound electronic displacement 74$b$ may be sufficiently perturbed (dE) on the spatial scale of an atom (dx) such that the electron may quantum-mechanically tunnel from its valence position 75$a$ to a free state 75$c$ without a gain in potential energy. When the electric field reverses, one-half cycle later (FIG. 2C), the now-displaced electron is pumped to a higher energy state relative to the energy of the valence shell as the slope of the electrical potential in free space 72$c$ and of the electrical potential of the non-free electron 74$c$ change. The electric-field reversal enables the high-potential energy free electron 75$d$ to fall back into the valence shell so as to once again become a bound electron 75$e$ with the liberation of a UV photon 77.

In the SFPI technique, the above-described process is interrupted after the second step (i.e., as shown in FIG. 2B) by application of a superimposed secondary electric field that causes sufficient physical separation of the free electron 75$c$ from the simultaneously-generated cation such that recombination does not occur. The superimposed secondary electric field is generated by high voltage applied to electrodes that are disposed in the vicinity of the path of the light pulse. The application of high voltage to such electrodes may be synchronized to the passage of the light pulses through the gas being ionized.

Conveniently, the SFPI technique can conveniently make use of conventional titanium-doped sapphire (Ti:sapphire) pulsed lasers that emit in the infrared (IR) or near-infrared (NIR) range of 650 to 1100 nm. Light within this wavelength range is much easier to generate and direct than is light of UV wavelengths. Further, photons within this IR to NIR wavelength range are of lower energy (individually) than photons of UV-visible wavelengths, thus rendering as less likely the competing ionization mechanism of multi-photon ionization. Accordingly, less ion fragmentation and a greater proportion of molecular ions or protonated molecules (cations) are expected using such IR-NIR wavelengths. The Ti:sapphire lasing medium is usually pumped with a pump laser that emits green light, such as an argon-ion laser or a frequency doubled Nd:YAG laser.

FIG. 3 is a schematic depiction of a known mass spectrometer ionization source 50, as taught in international (PCT) application publication WO 2013/098610 A1, that may employ the principle of strong-field ionization using a pulsed laser. The ionization source 50 can comprise an ionization chamber 12 for receiving an analyte of interest so as to expose the analyte to short laser pulses suitable for ionizing the analyte. The ionization chamber 12 can be connected to a mass spectrometer 14 (shown only partially) via an aperture 16 of a sampling cone 18 through which ions generated in the ionization chamber can pass to enter the spectrometer. The mass spectrometer can comprise one or more quadrupole ion guides and analyzers, such as the illustrated ion guide $Q_0$ that focuses and guides the ions entering through the aperture of the sampling cone to other stages of the mass spectrometer (not shown).

Still with reference to FIG. 3, the ionization chamber can comprise an annular metal holder 20 that is coupled to an electrically insulating section 22. The electrically insulating section 22 can comprise any of a variety of materials, including without limitation, ceramic, glass, or plastic. A channel 24 extends through the metal holder 20 into the ionization chamber 12 to provide a passageway for delivery of an analyte, which can be in a gaseous state, into the ionization chamber 12, e.g., via a buffer gas, such as helium. The sample can be the output of a gas chromatograph, a liquid chromatograph, or other source 25. Another channel 26 extends through the insulating section 22 into the ionization chamber to provide a passageway for delivery of a carrier gas into the ionization chamber to carry the generated ions to the aperture 16 of the sampling cone 18.

Still with reference to FIG. 3, a radiation-transmissive optical window 28 is coupled to the metal holder 20 and allows the passage of ionizing radiation 30 from an external radiation source 32 into the ionization chamber 12. The material from which the optical window 28 is formed can be selected based on the wavelength of the ionizing radiation 30 to allow the passage of that radiation into the chamber 12. A variety of radiation sources providing ionizing radiation can be employed. The radiation source 32 may provide short laser pulses, e.g., pulses having a pulse width in a range of about 2 femtoseconds to about 1 picosecond and may comprise, for example, a Ti:Sapphire laser configured to provide femtosecond pulses, e.g., pulses having a pulse width in range of about 2 fs to about 100 fs or a fiber laser configured to provide femtosecond pulses.

Still with reference to FIG. 3, a dichroic mirror 34 receives the radiation pulses generated by the radiation source 32 and reflects the radiation pulses onto a focusing objective 36 that in turn focuses the radiation pulses into a focal volume 38 (also referred to as the ionization volume) within the ionization chamber 12. A camera 40 can be positioned behind the dichroic mirror 34 to allow viewing the ionization chamber.

The SFPI method requires the provision of a light power density on the order of $10^{14}$ W/cm$^2$ (e.g., K Codling, L J Frasinki, Dissociative ionization of small molecules in intense laser fields, J. Phys. B: At. Mol. Opt. Phys. 26 (1993), pp. 783-809). Such power density may be achieved, with currently available lasers, in the vicinity of the focal region (beam waist from 10-100 µm) of a laser pulse of short duration (less than or equal to 150 fs). It has been shown that 100% of molecules within such a region may be ionized under such circumstances. Unfortunately, sample effluent streams (e.g., as introduced from a gas chromatograph column) are generally much larger than the size of the required focal region. For example, conventional GC columns emit an effluent plume from the entire cross section of a conventional lumen of 250 µm diameter. The diameter of the plume will generally expand after exiting the column. Thus, the ionization zone of any individual pulse comprises only a very small proportion of the analyte plume. The size of the ionization zone can be increased by reducing the pulse repetition rate of a laser so as to achieve greater energy per pulse without an increase in average laser power output. However, doing so causes a significant proportion of the total volume of an effluent plume to flow through the spatial profile of the zone at times when the laser is not emitting light.

SUMMARY

The inventors have recognized that a significant improvement in the efficiency of ion sources that employ strong field photo-ionization (SFPI) may be obtained by employing optical configurations that re-use each individual pulse emitted from a pulsed laser. Each such pulse is caused to pass through the effluent stream of a sample inlet device, such as but not limited to a gas chromatograph column, that inlets volatile samples to a mass spectrometer such that the single pulse causes repeated instances of ionization. Each instance of ionization generates ions within a different volume element of the effluent stream.

The multiple ionization instances of each pulse within ion sources in accordance with the present teachings are enabled by the provision of an optical cavity the optical pathway of which exists, at least partially, within an ionization chamber of a mass spectrometer which may be evacuated. The inventors here disclose two general optical cavity configurations that allow strong field photo-ionization (SFPI) using low cost ultrafast lasers. The first configuration includes various optical cavity designs that are able to "walk" the beam focus through the column exit cross section of a GC column. Such "off-axis" optical cavity designs include a set of optical focusing elements, preferably high reflectivity mirrors, that cause multiple folding of the path of a single pulse such that the pulse repeatedly focuses at successive positions that are not along the axis of the GC column or other sample inlet device. These "off-axis" designs provide significantly more spatial overlap between a laser with a small focus size and the GC-column effluent and may comprise an "open" design in which each pulse only makes a single circuit through the optical cavity.

The second configuration includes various "closed" cavity designs that maintain focus in the vicinity of the GC column exit for extended periods of time. Such closed-cavity implementations cause each optical pulse to make repeated round trips through the optical cavity—repeatedly traversing the same optical path in both forward and reverse directions. An optical switching assembly may be employed to first introduce a pulse into the cavity and then permit closed-cavity (i.e., repeated back-and-forth round trip) operation. The same or a different optical switching assembly may be later employed to remove the pulse from the optical cavity prior to the introduction of a subsequent pulse into the optical cavity. The closed cavity designs may be especially useful in systems with high peak power and low repetition rates. The ultra-short laser pulse is injected into the cavity and then extracted prior to the next injection.

The two optical cavity configurations listed above are not mutually exclusive. For example, a closed cavity may be configured to in an off-axis "walk-off" configuration that repeatedly focuses each optical pulse at a plurality off-axis positions during each round trip. The novel optical cavity designs disclosed herein include various designs that cause pulse trajectories to cross the effluent stream path at a high angle (such as a right angle). The novel optical cavity designs also include various alternative designs that cause pulse trajectories to assume trajectories that are substantially parallel or parallel to the effluent stream path at trajectory portions that overlap the effluent stream path. Such alternative optical cavity designs may include a cavity mirror having an aperture within which the GC column or other sample inlet device is disposed.

In accordance with the present teachings, the repeated focusing of each optical pulse causes repeated generation of positive ions and free electrons within an ionization zone in proximity to the beam waist and in an ionization chamber that may be at atmospheric pressure but is preferably maintained at sub-atmospheric pressure. The numerical apertures of the optical components are such as to cause the light pulses to diverge quickly in order to prevent damage to mirrors and other optical components. Ambient pressures of less than $10^{-5}$ Torr limit ion fragmentation that would otherwise be caused by collision of ions with neutral molecules. In accordance with the present teachings, electrodes are provided to generate an extraction electric field that separates the positive ions from free electrons, thereby preventing recombination that would otherwise re-form neutral molecules. According to some embodiments, the extraction electric field may itself be pulsed in synchronization with the laser pulses.

In a first aspect in accordance with the present teachings, an ion source for a mass spectrometer is disclosed, the ion source apparatus comprising: an evacuated chamber having an interior receiving a gaseous sample effluent stream; a source of light pulses of pulse width 150 femtoseconds or less; a window of the evacuated chamber through which the light pulses pass into the evacuated chamber interior; one or more mirrors within the evacuated chamber disposed such that the light pulses are reflected from each of the one or more mirrors such that the reflected pulses are caused to focus at one or more focal regions within the effluent stream within the evacuated chamber interior; and a pair of electrodes disposed at opposite sides of the one or more focal regions.

In another aspect in accordance with the present teachings, a method of ionizing a sample for mass analysis by a mass spectrometer is disclosed, the method comprising: introducing a gaseous effluent stream of the sample into an interior of an evacuated chamber; causing a plurality of light pulses to be focused within a path of the effluent stream within the evacuated chamber, wherein each light pulse is caused to be focused within the path of the effluent stream a plurality of times such that positive ions of the sample are generated during each focusing; and causing at least a portion of the positive ions to migrate towards and into an inlet aperture of the mass spectrometer.

BRIEF DESCRIPTION OF THE DRAWINGS

The above noted and various other aspects of the present invention will become apparent from the following description which is given by way of example only and with reference to the accompanying drawings, not necessarily drawn to scale, in which.

DETAILED DESCRIPTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. To fully appreciate the features of the present invention in greater detail, please refer to FIGS. 1-13, in which like reference numbers refer to like elements, in conjunction with the following discussion.

The electric field generated by a laser beam is given by:

$$E(r, z) = \sqrt{\frac{2}{\varepsilon_0 c} I(r, z)} \quad \text{Eq. (1)}$$

where I(r,z) is the intensity in Watts per square centimeter. For a focused Gaussian beam:

$$I(r, z) = I_0 \left(\frac{w_0}{w(z)}\right)^2 \exp\left(\frac{-2r^2}{w^2(z)}\right) \qquad \text{Eq. (2)}$$

where $$I_0 = \frac{2P}{\pi w_0^2},$$

and P is power in Watts. In the axial dimension (z-axis) the radial beam waist, w(z) is given by:

$$w(z) = w_0 \sqrt{1 + \left(\frac{z}{z_R}\right)^2} \qquad \text{Eq. (3)}$$

where $$z_R = \frac{\pi w_0^2}{\lambda}$$

and $\lambda$ is wavelength in μm. The quantity $z_R$ is typically referred to as the Rayleigh length, the distance at which the cross sectional area of a focused beam doubles.

Figure 1:
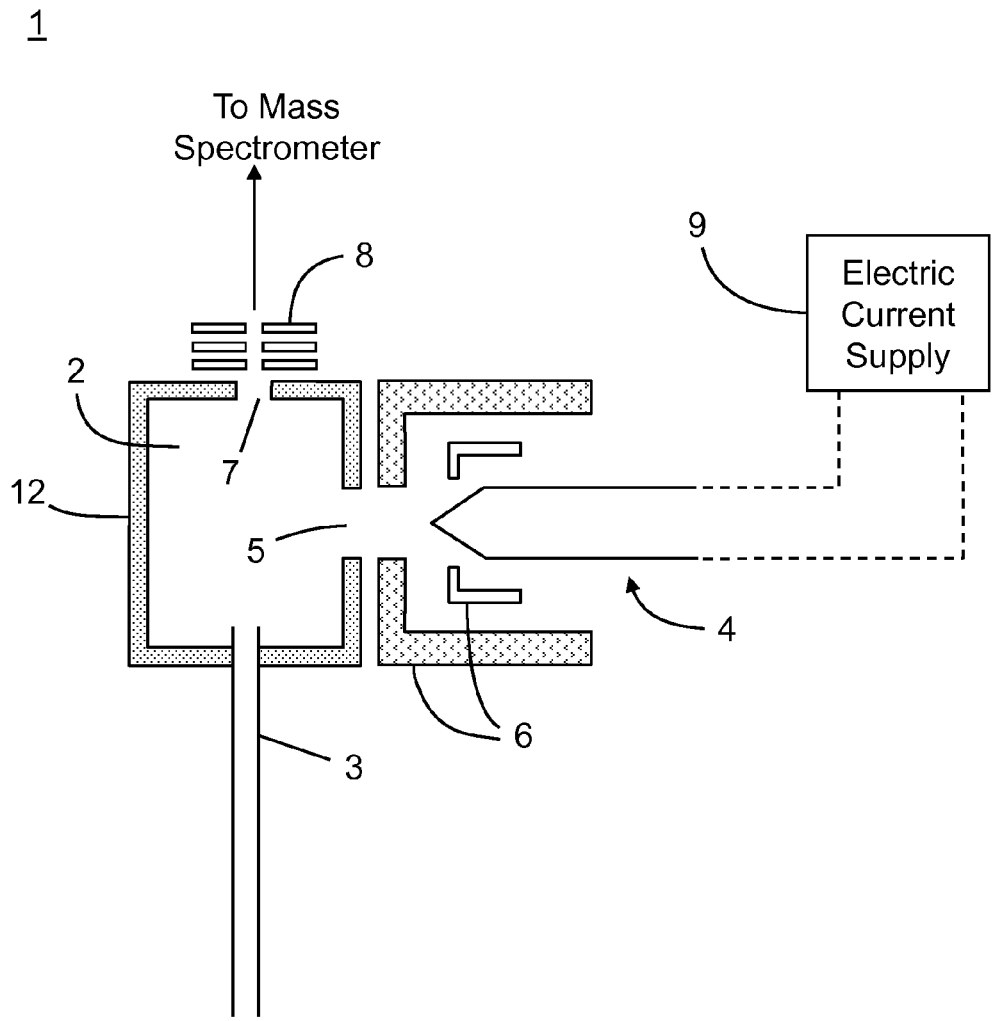
FIG. 1 is a schematic diagram of a conventional electron ionization (EI) ion source.
Figure 2A:
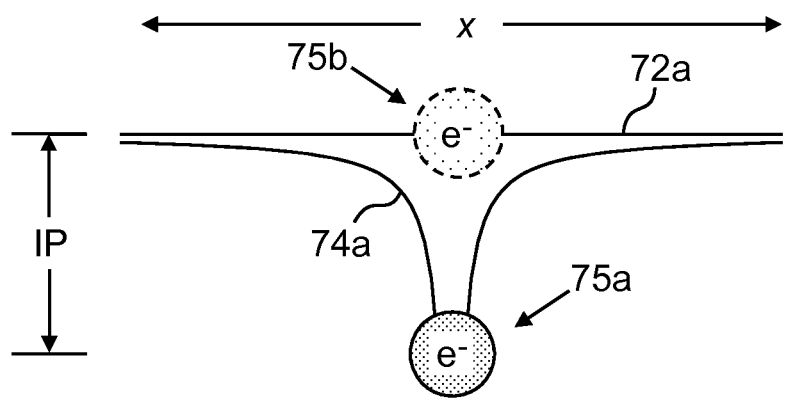
FIG. 2A is a schematic depiction of a ground energy state of a valence electron of a molecule and an ionization potential of the molecule in the absence of an externally applied electric field.
Figure 2B:
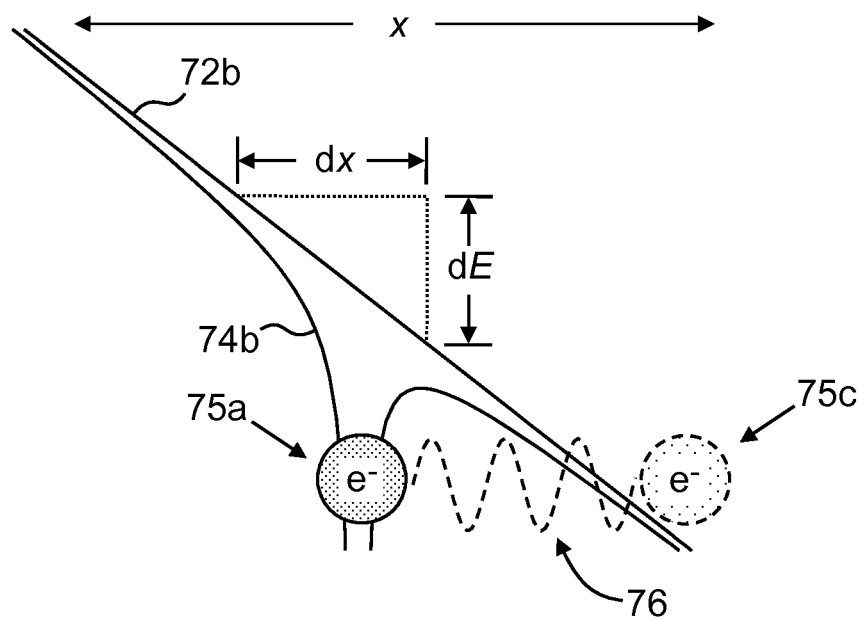
FIG. 2B is a schematic depiction of a ground state of a valence electron of a molecule and a lowest energy state of a valence electron liberated from the molecule in the presence of a strong externally applied electric field.
Figure 2C:
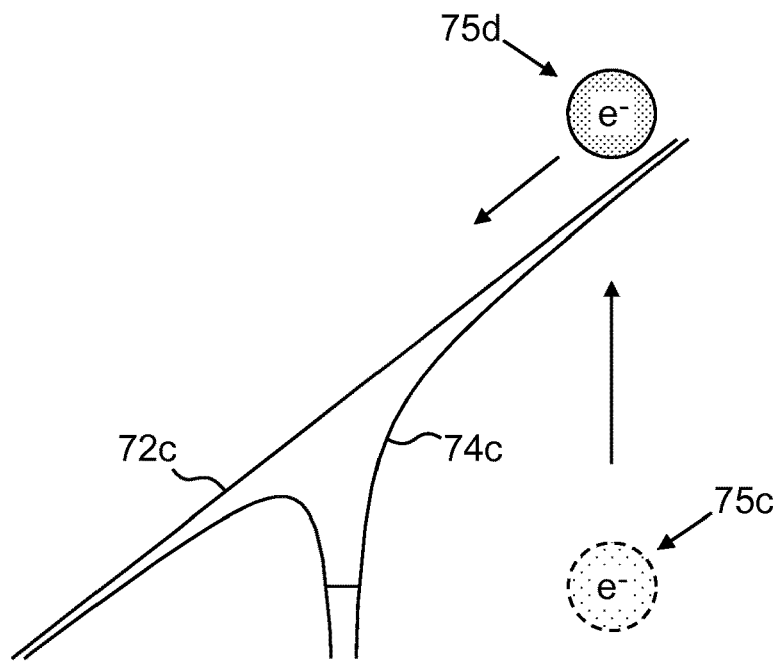
FIG. 2C is a schematic depiction of acceleration, by an externally applied electric field, of a free electron away from a positive ion generated by liberation of the electron from a molecule caused by the field.
Figure 2D:
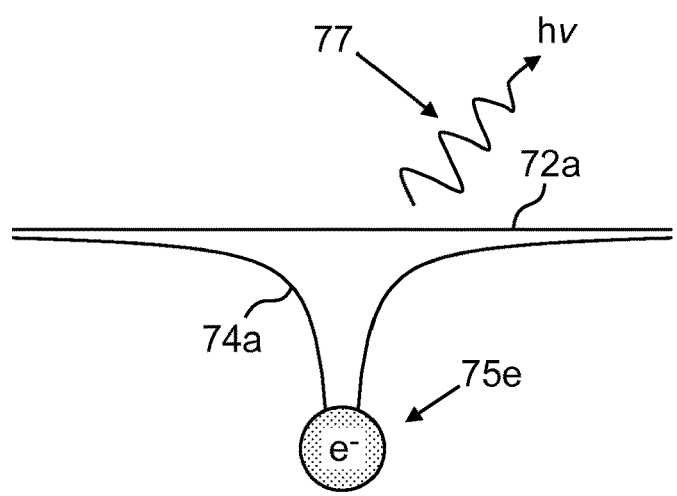
FIG. 2D is a schematic depiction of recombination of a free electron with a positive ion so as to liberate a photon upon removal of a transient external electric field.
Figure 3:
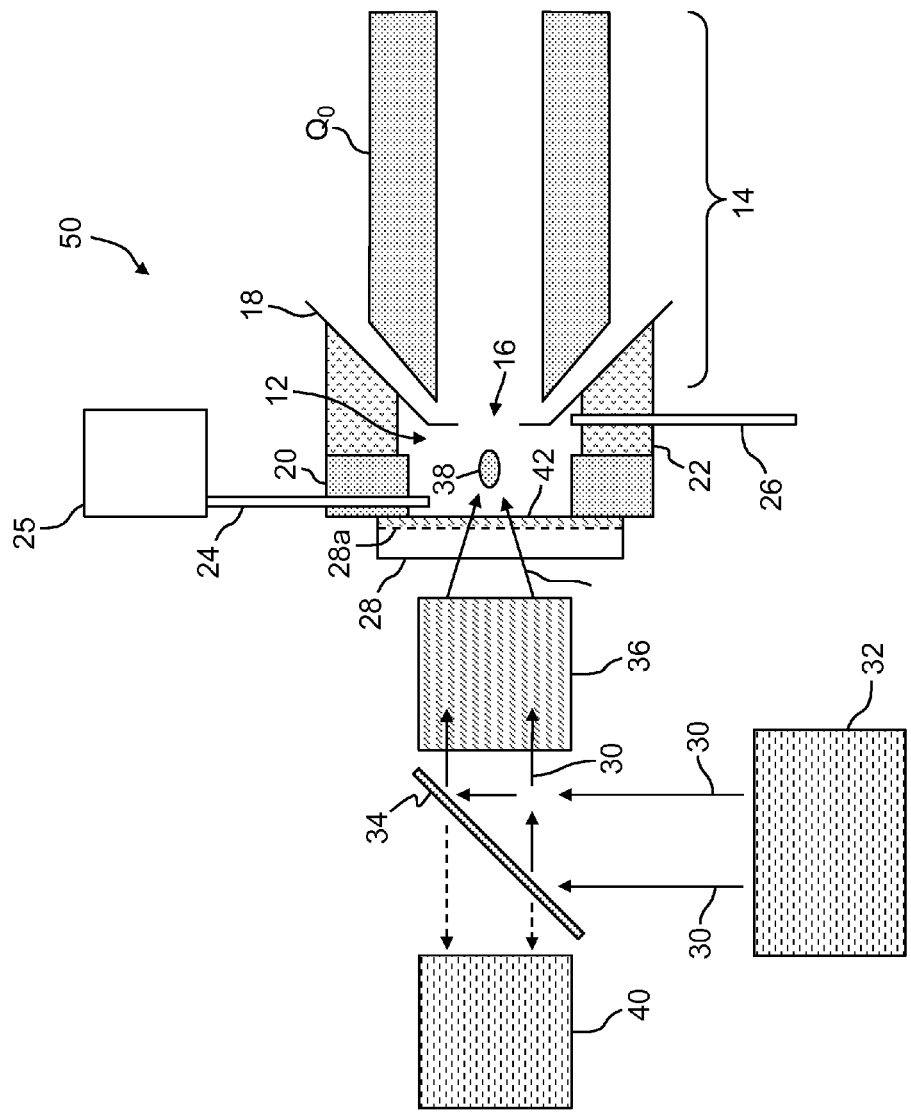
FIG. 3 is a schematic of a known mass spectrometer comprising an ion source that generates ions by the principle of strong field photo-ionization using a pulsed laser.
Figure 4:
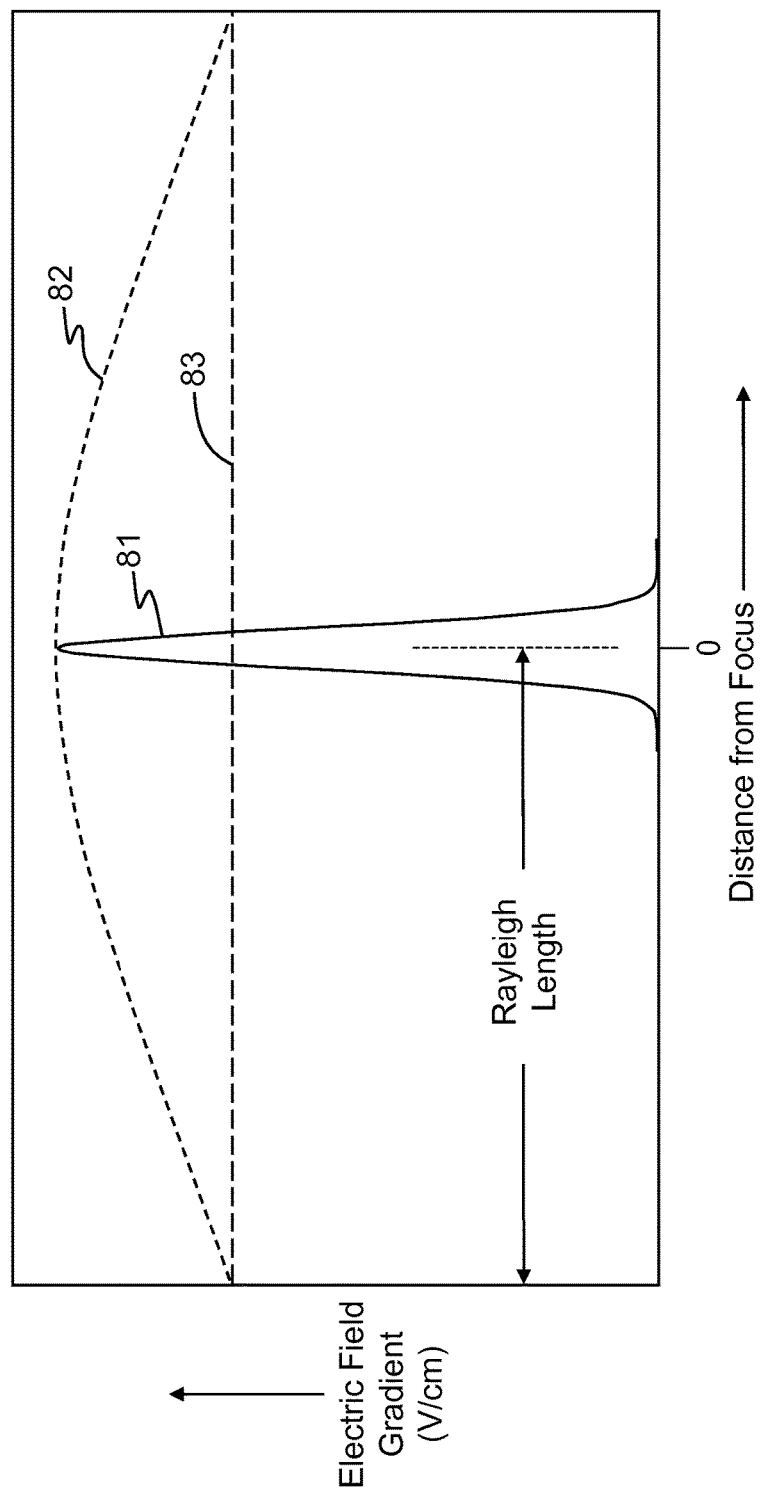
FIG. 4 is a schematic graph of the variation of electric field gradient of a focused laser light versus distance from the focal point as taken parallel to the light propagation direction (short-dashed line) and perpendicular to the laser propagation direction (solid line) and also showing the minimum electric field gradient (horizontal long-dashed line) required for ionization assuming that the laser power is such that ionization occurs just within one Rayleigh length of the focal point.

Using the equations above and selecting the power, wavelength, and focus so that the minimum ionization field gradient is achieved at the Rayleigh length results in the relationships shown in FIG. 4 in which the electric field gradient of a focused laser light is plotted versus distance from the focal point, indicated as "0" on the horizontal axis. The short-dashed line 82 in FIG. 4 is a plot of the electric field gradient as taken parallel to the light propagation direction (i.e., along the z-axis) and the solid line 81 is a plot of the electric field gradient as taken in a radial dimension (i.e., perpendicular to the z-axis). Under the assumption that the laser power is such that ionization occurs just within one Rayleigh length of the focal point, then the horizontal long-dashed line 83 gives the minimum electric field gradient required for ionization.

The calculated electric-field gradient values shown in FIG. 4 may be used to define a volume of ionization (the "ionization volume") created by the focused spot. Accordingly, the ionization volume can be approximated as a cylinder whose aspect ratio, length divided by diameter, is a function of the focused beam waist, $w_0$, and the wavelength, $\lambda$. The ionization volume may thus be defined as:

$$V(w_0, \lambda) = \pi^2 \ln(2) \left(\frac{w_0^4}{\lambda}\right) \qquad \text{Eq. (4a)}$$

or, in terms of laser power, P, and intensity, I, as $$V(P, I_0, \lambda) = 4\ln(2) \left(\frac{P^2}{\lambda I_0^2}\right) \qquad \text{Eq. (4b)}$$

For a given minimum ionization target and a fixed wavelength laser, the ionization volume is proportional to the laser power squared.

Figure 5A:
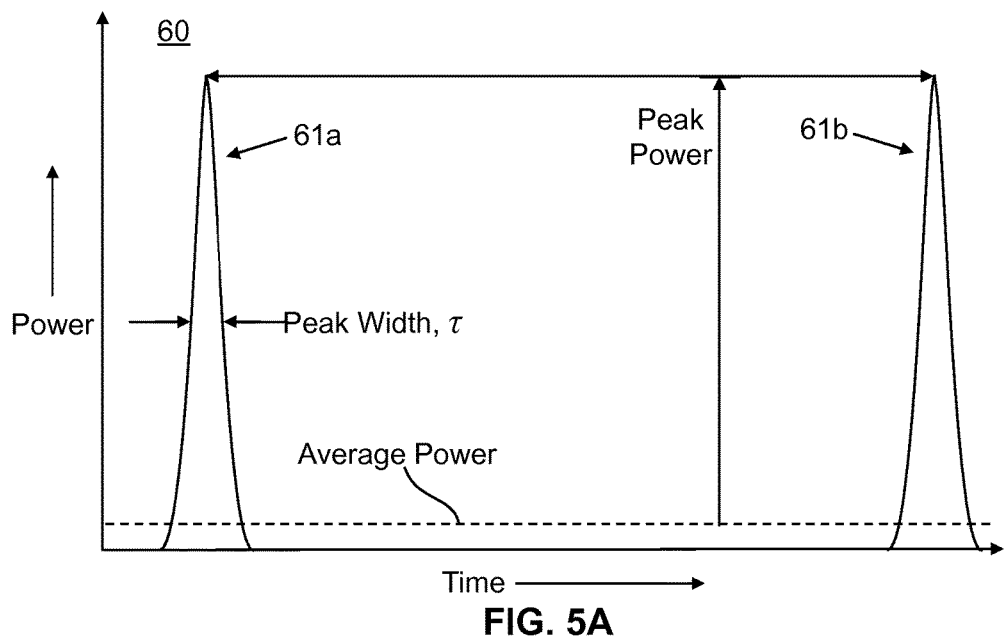
FIG. 5A is a schematic graph of emitted power versus time corresponding to two emitted pulses of a pulsed laser, illustrating general relationships between peak power, average power and pulse width.

There is a natural tradeoff between repetition rate (f) and peak power ($P_{peak}$). In a pulsed femtosecond laser, the average power is compressed into a narrow pulse width ($\tau$) that is associated with a high peak power. The relationship between peak power and average power is given by $$\left(\frac{P_{peak}}{P_{ave}}\right) = \left(\frac{0.94}{f\tau}\right) \qquad \text{Eq. (5)}$$

and is diagrammed schematically in FIG. 5A in which two separate pulses 61a, 61b are shown and the separation time between the pulses is (1/f). The graph 60 of FIG. 5A is highly schematic; in general, the ratio between the time separation between pulses and the peak width, $\tau$, will be much greater than is implied by this figure.

Figure 5B:
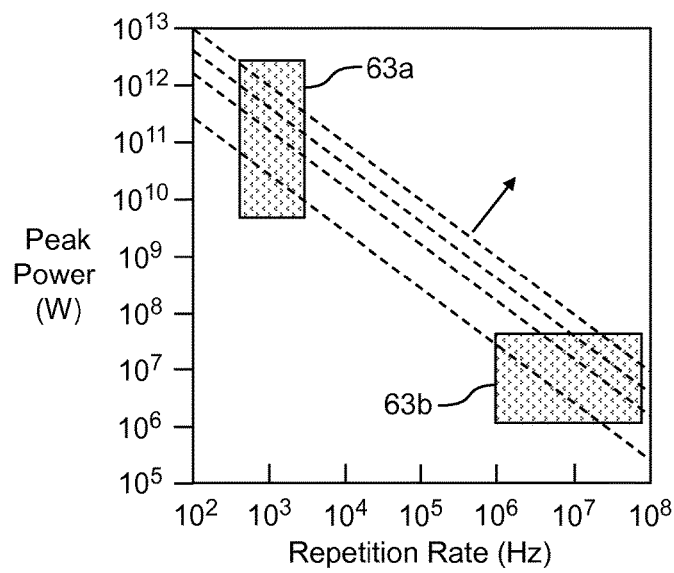
FIG. 5B is a graphical depiction of the performance ranges of available femtosecond lasers.

FIG. 5B depicts the performance ranges of available so-called "femtosecond" pulsed Ti:sapphire lasers as of the time of writing of this document, in terms of available repetition rate (in hertz, Hz) and peak power (in watts, W). Commonly available femtosecond lasers that can be employed in conjunction with the present invention use typical pulse widths of 25-150 fs. Lasers having pulse widths as short as 2 fs may also be used. The performance range of available commercial-grade lasers, which are conventionally employed for laser machining purposes, is indicated by box 63b. The performance range of the more-costly research-grade lasers is indicated by box 63a. The diagonal dashed lines are isopleths of constant average power, which increases in the direction of the arrow shown in FIG. 5B.

To achieve the electric field gradient required for SFPI, the peak power at the focus must exceed 150 Mega-Watts for a tightly focused laser, and can exceed 10 Giga-Watts for larger laser focuses. This corresponds to a peak power density of approximately $10^{14}$ W/cm$^2$ that is required to ionize molecules in accordance with the principles of SFPI described above. The inverse relationship between peak power and the product of frequency and pulse width as indicated by Eq. (5) has limited the effectiveness of SFPI historically, due to the high cost of laser power in the femto-second pulse regime. Fortunately, micromachining and medical imaging applications continue to drive down the cost of these types of lasers.

Laser pulse power density may be increased to the level required for ionization by choosing optics that bring the pulses to a tight focus. However, a tight laser focus can cause difficulties in beam pointing and alignment. Conventionally, there are two main options for increasing the power density to the required level: (a) increasing the average power of the laser (b) reducing the repetition rate of the laser. The first option (a) is the conventional technique used to construct fs lasers for research purposes. Unfortunately, pump lasers required to generate high average powers (e.g., greater than about 1 W) are very expensive. Reducing the repetition rate (option b) allows the peak power to be increased until breakdown thresholds begin to limit the process. The inventors therefore consider that reduction in the repetition rate is valuable as a means for reducing the average power and cost requirements of the laser for general use.

Figure 6B:
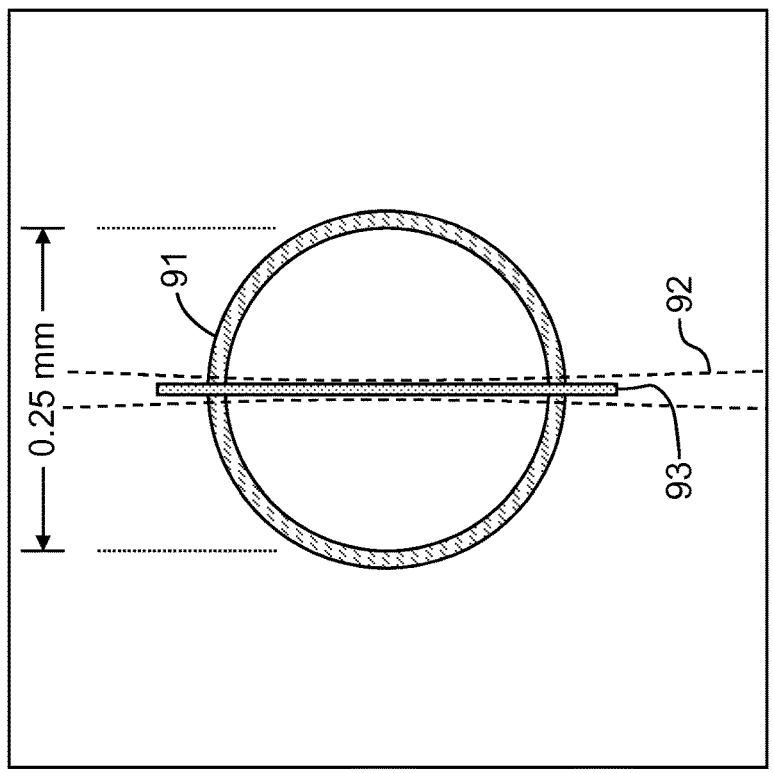
FIG. 6B is a second schematic view of the path of the focused light beam or pulse as viewed towards the exit end of the column and along the axis extended of the column and also showing the expected ionization volume for a pulsed laser having an average power of 10 Watts and a 7.7 µm beam waist.
Figure 6A:
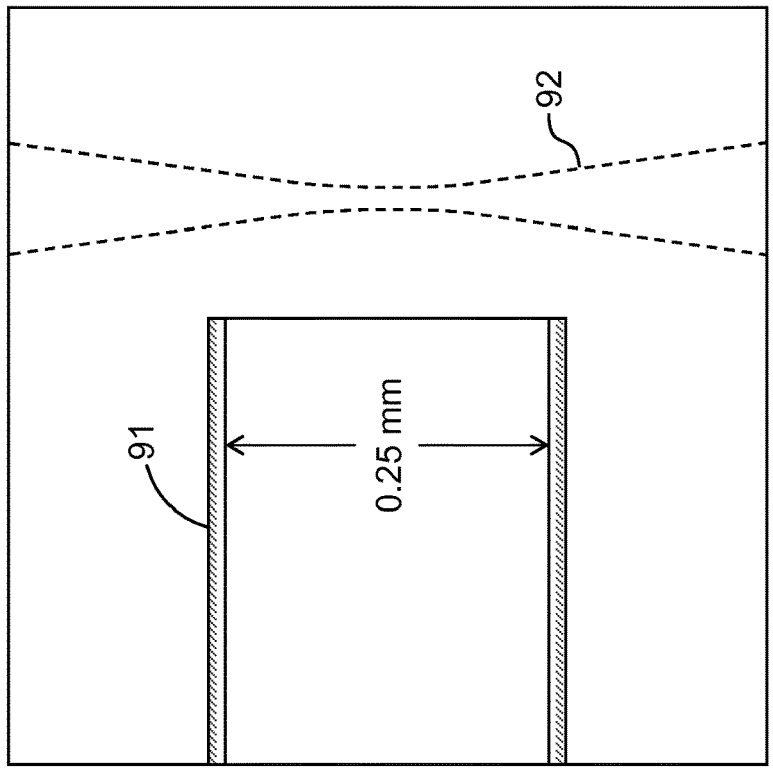
FIG. 6A is a schematic diagram showing the path of a focused light beam or pulse across the path of effluent emerging from a typical gas chromatography column having a typical inner diameter of 0.25 mm.
Figure 7:
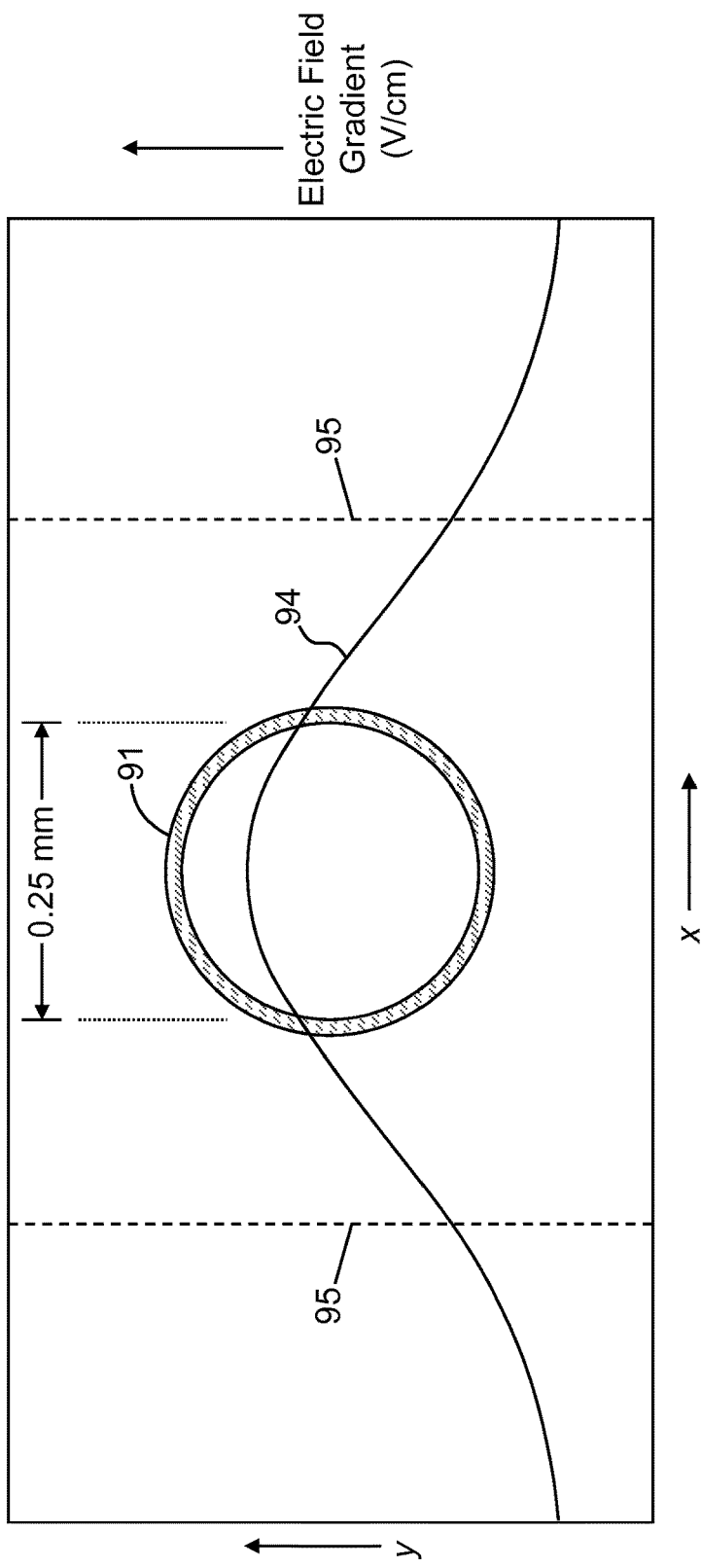
FIG. 7 is an end-on view of the aperture of an 0.25 mm inner diameter column showing the position of the beam profile (vertical dashed lines) and a superimposed graph of the normalized electric field gradient (solid line) versus position relative to the column for a pulse emitted from a commercially available laser operating at 10 kHz repetition rate and 6 W average power and focused to a 200 µm beam waist.

FIGS. 6A, 6B and 7 illustrate examples of the above trade-offs and considerations applied to operation of an ion source for a mass spectrometer. A femto-second laser is operated with a relatively low repetition rate ranging from 1-10 kHz. FIGS. 6A-6B illustrate a typical GC column 91, 0.25 mm ID, relative to a laser beam 92 with an average power of 10 Watts resulting, for this example, in a 7.7 μm beam waist using a laser operated at 100 kHz. The resulting ionization volume (estimated by rectangle 93) only covers approximately 6% of the total GC column effluent. From Eq. (5), the peak power can be increased by reducing the operating frequency and, given that the peak power and necessary beam waist are inversely proportional, this results in a larger required focus. As another example, if a laser is operated at 5 kHz with an average power of 4 W, the required focus is 46 μm. This results in a 23% ionization efficiency due to the overlap of the laser cross section and the GC column effluent. Additionally the amount of time the GC effluent is within the laser cross section must be considered. At 5 kHz, only 32% of the GC column effluent experiences the laser potential before moving out of the ionization region between pulses. This reduces the total ionization efficiency to approximately 7%. Despite increasing the peak power of the laser to achieve a focused beam waist six times larger than the original example, the ionization efficiency only improves by 1% due to the reduced repetition rate.

If the relationship between peak power and repetition rate is driven to extreme levels (near breakdown thresholds for optics and ionization in air), a laser can be produced which can achieve the required electric field gradient at a focus of several hundred μm, but with a very low repetition rate. For example, a laser with a 10 Hz repetition rate can produce the required electric field gradient with a focus of 350 μm at an average power of only 100 mW. This is advantageous due to the low average power required, but also because the larger focus reduces the sensitivity to beam pointing drift. However, the larger focus also requires a relatively long flight path of the laser pulses between the focus and the nearest optical components in order to avoid laser damage to those components. Also, the extremely low repetition rate results in a 0.5% ionization efficiency because molecules travel through the ionization region between laser pulses.

Another example is given below (FIG. 7) for a commercially available laser operating at 10 kHz repetition rate and 6 Watts average power. The image above shows a simulation of a beam waist that has been increased to 200 μm and the resulting electric field gradient is sufficient to ionize 100% of the column effluent as the pulse travels past the column. Unfortunately, the repetition rate required to achieve this spot size results in roughly 66% of the column effluent traveling past the ionization region between pulses. The resulting ionization efficiency is reduced to 30%.

The above examples illustrate that, in addition to the expected tradeoffs between peak power and beam waist size and between peak power and pulse repetition rate, there is a further trade-off between pulse repetition rate and the volume of effluent that is in the beam path during passage of a laser pulse. To improve the ionization efficiency, the inventors have recognized that a reflection cavity can be used so to as to enable re-use of each individual pulse. The following discussions disclose embodiments of novel ion source designs that make use of such reflection cavity configurations.

Figure 8A:
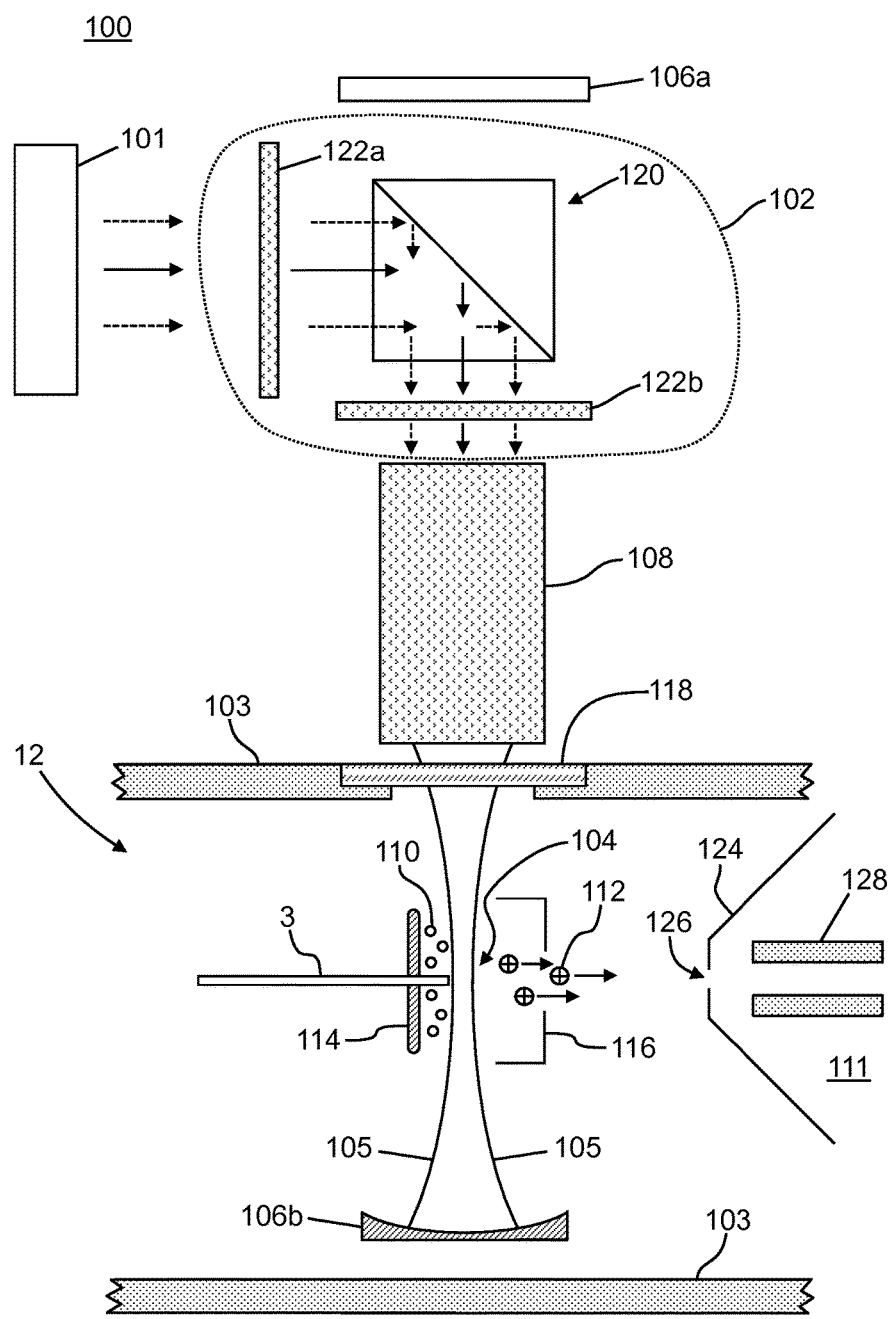
FIG. 8A is a schematic depiction of a first ion source for a mass spectrometer in accordance with the present teachings, showing introduction of a laser pulse into an optical cavity of the ion source.
Figure 8B:
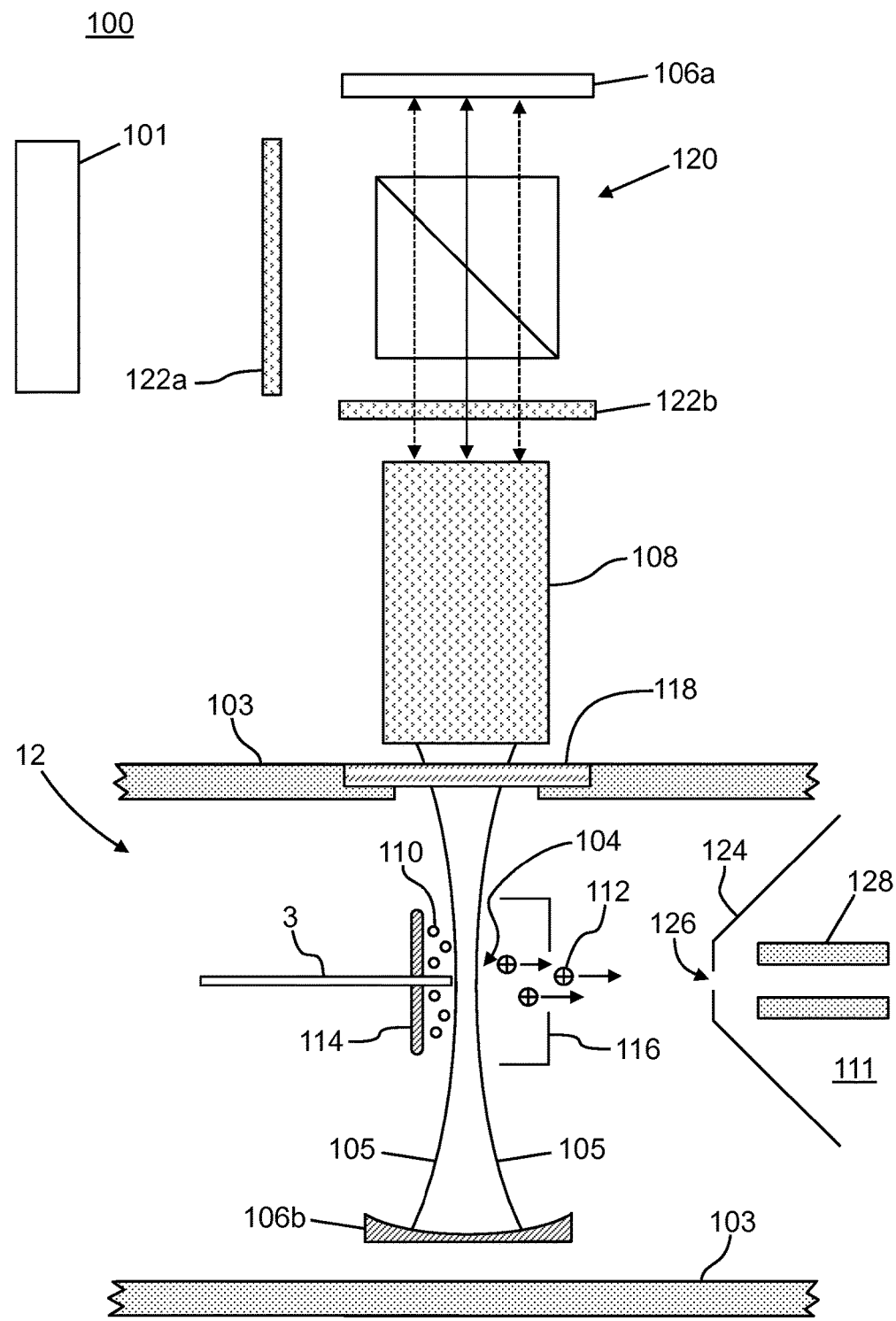
FIG. 8B is a schematic depiction of the ion source of FIG. 8A, schematically showing repeated back and forth propagation of light corresponding to a single laser pulse within the cavity and across the path of effluent emerging from a chromatographic column.

FIGS. 8A-8B are schematic depictions of a first ion source 100 for a mass spectrometer in accordance with the present teachings. The ion source 100 includes an optical cavity, defined between first mirror 106a and second mirror 106b that is partially disposed within an evacuated ionization chamber 12 within housing 103 of a mass spectrometer (only partially illustrated in FIGS. 8A-8B). The ion source 100 is designed such that a high-peak-power optical pulse from a pulsed laser source 101 can be admitted into the optical cavity in a controlled fashion and such that the optical pulse can, after admission into the optical cavity, reflect multiple times between the first and second mirrors 106a, 106b. The ion source 100 also provides for removing the optical pulse from the optical cavity after residing for a certain time within the cavity.

The admission of the optical pulse into the cavity and removal of the pulse from the cavity are enabled by the provision of an optical switching device or assembly 102 included at least partially within the optical cavity. In the illustrative embodiment illustrated in FIGS. 8A-8B, the optical switching device or assembly 102 comprises a polarization beam splitter 120 and first and second switchable polarization controlling elements 122a, 122b, with the polarization beam splitter and second switchable polarization controlling element 122b disposed within the optical cavity and the first polarization controlling element 122a disposed between the polarization beam splitter and the laser 101. Switchable polarization rotators (for example, electro-optic modulators) are known which are able to change the angle of polarization of light passing therethrough by an electrically controlled change in birefringence. As will be understood by one of ordinary skill in the optical arts, other forms or configurations of an optical switching device or assembly could alternatively be employed.

As illustrated in FIGS. 8A-8B, the ion source 100 further comprises a lens or lens assembly 108 which causes an initially collimated laser light pulse to focus to a beam waist 104 in proximity to the outlet end of a gas chromatograph column 3, thereby causing ionization of eluate molecules within an ionization zone by the principles of strong-field photo-ionization as previously described. Advantageously, the lens or lens assembly 108 may be provided as an achromat microscope objective. The light pulse is transmitted into ionization chamber 12 through an optical window 118 that forms an airtight seal against housing 103. The peak power of the optical pulse is such that the electric field gradient within the ionization zone causes electrons to be ejected from eluate molecules within the ionization zone, thus creating a region of plasma comprising free electrons 110 and eluate cations 112. After passing through the beam waist 104, the optical pulse 105 expands until it encounters the second mirror 106b which may be formed in the shape of a spherical cap so as to refocus the reflected pulse at the same beam waist position—that is, at the position of the beam waist prior to reflection.

The electrons 110 formed by the strong-field photo-ionization are separated from the eluate cations 112 by a pair of electrodes 114, 116 that are electrically positively and negatively biased, respectively. The negatively biased electrode 116 is disposed between the beam waist 104 and an inlet aperture 126 of a sampling cone 124 of the mass spectrometer so as to cause a flow of the cations towards the mass spectrometer through one or more gaps in the electrode 116. The cations may be accelerated into a lower-pressure chamber 111 mass spectrometer through the inlet aperture 126 by the applied electrical potential difference between the electrodes 114, 116 as well as by a possible additional electrical potential difference between the sampling cone 124 and the electrode 116. The cations are then guided within the lower-pressure chamber 111 by ion optical element 128 such as a multipole ion guide. The positively biased electrode 114 is disposed on the opposite side of the beam waist from the mass spectrometer, thereby causing the free electrons to migrate towards the electrode 114 at which they are neutralized.

FIG. 8A illustrates a configuration of the ion source 100 in which a laser pulse is introduced into the optical cavity of the ion source. In the pulse introduction configuration illustrated in FIG. 8A, the optical switching device or assembly 102 is configured so as to deflect the light pulse issued from laser 101 (depicted by arrows) into and through the optical lens or lens assembly 108 and into ionization chamber 12 through optical window 118. The light of the laser pulse is naturally polarized and, according to exemplary pulse introduction configuration illustrated in FIG. 8A, the polarization beam splitter 120 is disposed so as to deflect light that is polarized parallel to the laser pulse polarization direction towards the optical lens or lens assembly 108. Further according to the configuration illustrated in FIG. 8A, the first polarization controlling element 122a is configured so as to transmit the light pulse therethrough without polarization rotation so that the pulse may be deflected at the polarization beam splitter 120 as shown in FIG. 8A.

FIG. 8A further illustrates that, after deflection, the deflected light pulse then passes into ionization chamber 12 through the second polarization controlling element 122b, the optical lens or lens assembly 108 and optical window 118. The second polarization-controlling element 122b may be configured at this time so as to rotate the polarization direction of the deflected light pulse by ninety degrees. In accordance with the well-known operation of the polarization beam splitter 120, the so-rotated polarization is such that the light pulse will be transmitted straight through the polarization beam splitter, without deflection, upon the next encounter of the pulse with the polarization beam splitter.

FIG. 8B illustrates an alternative configuration of the polarization controlling element 122b of the ion source 100 in which a previously introduced laser pulse is caused to traverse a plurality of round trips through the optical cavity that is defined by the first mirror 106a and the second mirror 106b. After initial introduction of the pulse into the ionization chamber 103, the pulse profile focuses to a beam waist 104, and then expands again until it reaches the second mirror 106b. The second mirror 106b is designed to as to reflect the pulse back through the optical cavity in the opposite direction. Preferably, the reflected pulse is caused to re-focus to a beam waist 104 and then exit the ionization chamber 12 through window 118. The reflected pulse spatially diverges after passing through beam waist 104; the lens or lens assembly 108 re-collimates the light pulse that then passes into and through the second polarization-controlling element 122b.

Still with reference to FIG. 8B, if the second polarization controlling element 122b was configured to rotate the pulse polarization direction upon introduction of the pulse into the optical cavity (FIG. 8A) then, upon passage of the reflected pulse through the second polarization controlling element 122b, this element is configured so as to not further rotate the pulse polarization direction. Otherwise, the second polarization-controlling element 122b is configured to rotate the polarization by ninety degrees such that the reflected pulse passes straight through the polarization beam splitter, without deflection, to the first mirror 106a. The first mirror 106a then reflects the pulse back into the optical cavity for a second round trip through the cavity. As a result of the prior polarization rotation, the doubly-reflected pulse once again passes straight through the polarization beam splitter 120, without deflection, in the direction of the second polarization controlling element 122b and the lens or lens assembly 108.

During the second and subsequent round trips through the optical cavity, the second polarization-controlling element 122b is configured so as to not rotate the pulse polarization direction. As a result, during each round trip, the pulse passes undeflected through the polarization beam splitter 120 (as indicated by the double-headed arrows) and the pulse remains within the cavity. While the pulse is making round trips through the cavity, the first polarization controlling element 122a may be configured so as to rotate, by ninety degrees, the polarization direction of polarized light so that any light that may be emitted from the laser during this time passes straight through the polarization beam splitter without deflection and does enter the optical cavity defined by the two mirrors. After a certain time period within the optical cavity or after a certain number of round trips therethrough, the optical switching device or assembly 102 is reconfigured as shown in FIG. 8A, such that the pulse is removed from the cavity in the reverse direction from that in which it was introduced into the cavity. An additional beam-deflecting element (not shown) may be disposed between the laser 101 and the optical switching device or assembly 102 so that the removed pulse light does not interfere with the operation of the laser.

Figure 9:
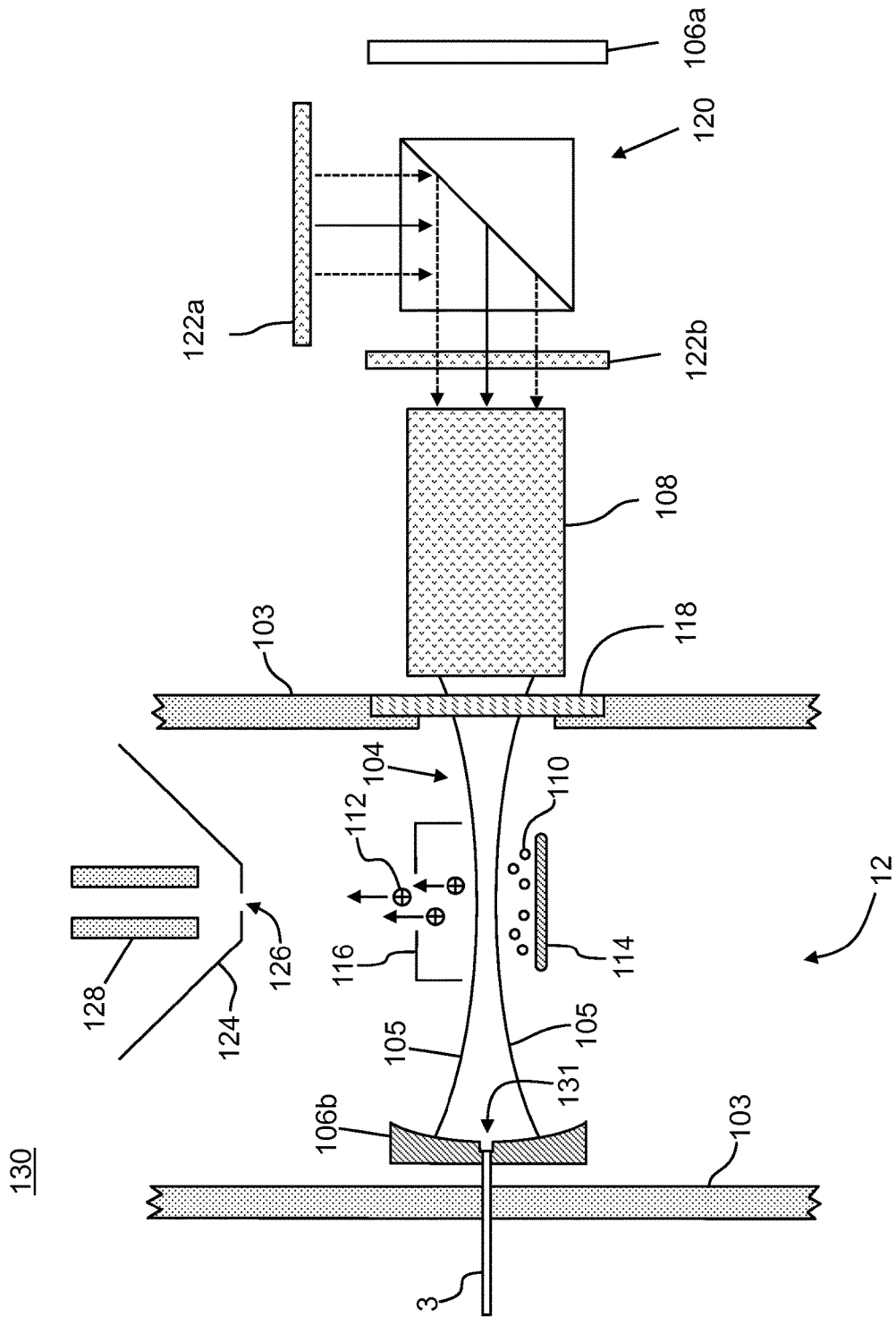
FIG. 9 is a schematic depiction of a second ion source for a mass spectrometer in accordance with the present teachings, showing introduction of a laser pulse into an optical cavity of the ion source.

FIG. 9 is a schematic depiction of a second ion source 130 for a mass spectrometer in accordance with the present teachings. The ion source 130 includes all of the components previously described with reference to the ion source 100 shown in FIGS. 8A-8B. Most of these similar components, which are numbered similarly as in FIGS. 8A-8B, are not re-described in detail here. The main difference between the ion source 130 (FIG. 9) and the ion source 100 (FIGS. 8A-8B) is that, whereas the pathway of the laser pulse crosses the axis extended of the GC column 3 at substantially a right angle in the ion source 100, this pathway is substantially parallel to the GC column axis extended in the ion source 130. In this context, the term "substantially parallel" implies an angle of zero degrees plus-or-minus five degrees. The geometric configuration shown in FIG. 9 is provided by providing the outlet end of the GC column within an aperture 131 of the second mirror 106b. The distance between the beam waist 104 and the second outlet end of the GC column 3 is such that the expansion of the profile of the optical pulse 105 between the beam waist and the GC column prevents the occurrence of laser damage to the column end, at the maximum working energy per pulse within the optical cavity. To enhance the distance between the GC column 3 and the beam waist 104, the outlet end of the column may be recessed away from the reflective surface of the mirror 106b within the aperture 131 as shown in FIG. 9.

Figure 10A:
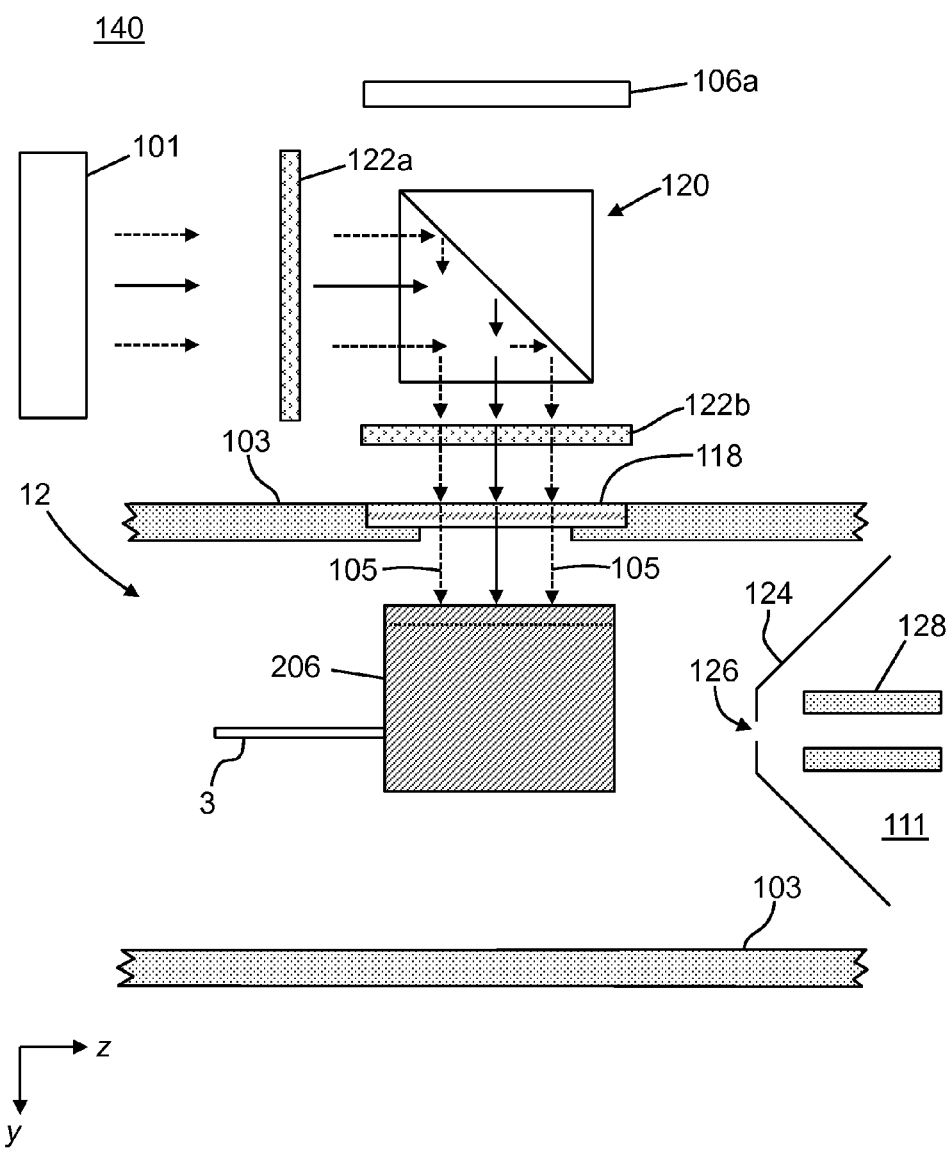
FIG. 10A is a schematic longitudinal view of a third ion source for a mass spectrometer in accordance with the present teachings.
Figure 10B:
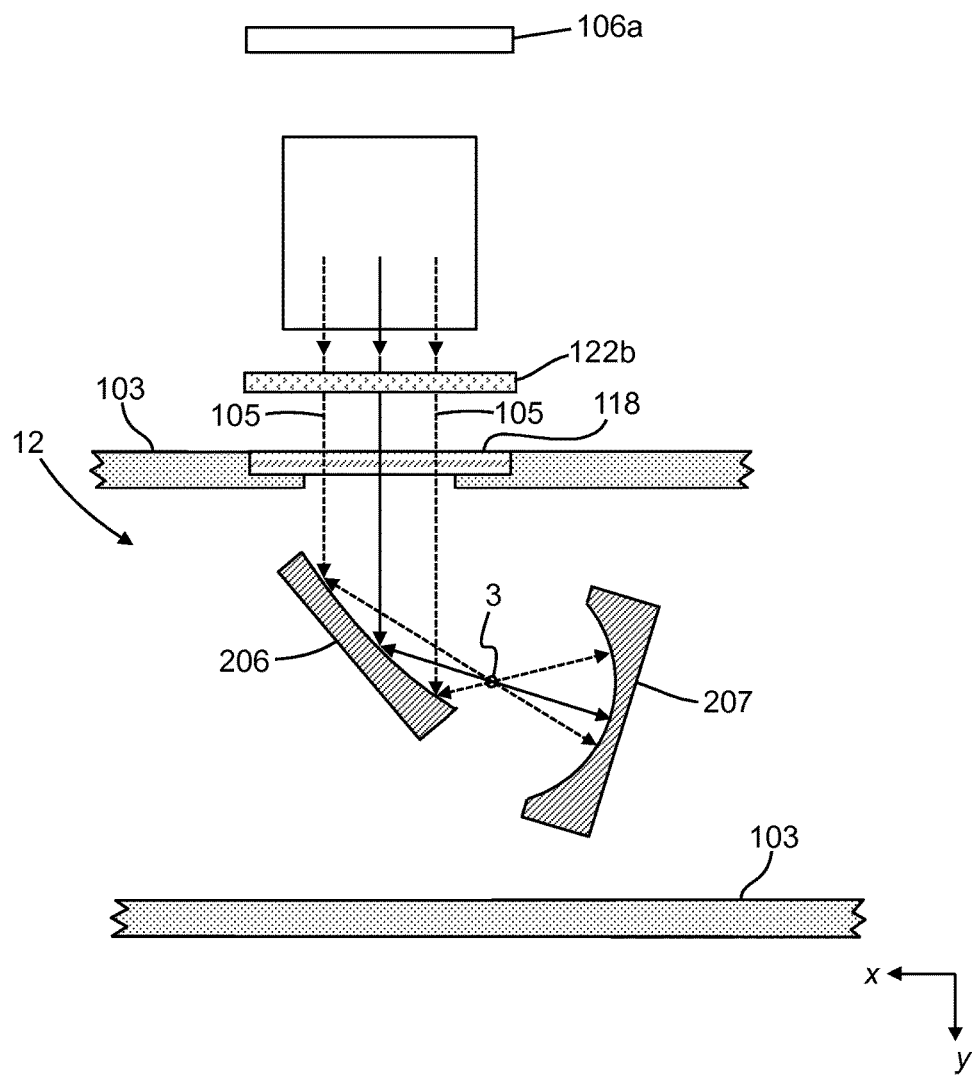
FIG. 10B is a schematic transverse view of the third ion source illustrated in FIG. 10A.

FIGS. 10A-10B are schematic longitudinal and transverse views of a third ion source for a mass spectrometer in accordance with the present teachings. FIGS. 10A and 10B, taken together, indicate the orientations of spatial x, y and z axes so that the orientations of the two drawings may be related to one another. The ion source 140 differs from the ion sources described supra in that the ion source 140 does not include a focusing element disposed outside of the ionization chamber 12. Instead a collimated light pulse 105 (e.g., as emitted from a laser) is passed into the ionization chamber 12 through the single window 118. The collimated light of the pulse 105 is then brought to a focus at a beam waist disposed adjacent to the outlet end of a gas chromatograph column 3 by a focusing element that is within the ionization chamber 12.

In the exemplary embodiment illustrated in FIGS. 10A-10B, the focusing element of the ion source 140 comprises an off-axis paraboloid-segment reflector 206 that, in the present example, is specifically a first-surface mirror of which the reflective surface is a concave segment of a geometric paraboloid. The reflector 206 is disposed within the ionization chamber 12 so as to intercept the collimated light transmitted through the window 118 and cause it to focus at the vertex of the paraboloid of which the reflective surface of reflector 206 is a segment. After passing through the beam waist, the light of the pulse diverges. The divergent light is then retro-reflected back to the focal point and to the reflector 206 by spherical mirror 207 that, in the present example, is specifically a first-surface mirror of which the reflective surface is a concave spherical cap. The spherical center of the spherical cap is coincident with the focal point of the off-axis paraboloid-segment reflector 206.

The mirror 106a and spherical mirror 207 of the ion source define an optical cavity within which a laser light pulse 105 may propagate, both backward and forward, a plurality of times. The laser light pulse may be introduced into the optical cavity by the process and means described supra with reference to FIG. 8A. Subsequently to such introduction into the optical cavity, the laser light the laser light pulse is twice brought to a focus in proximity to the outlet end of a gas chromatograph column 3. Provided that the energy of the pulse is not degraded during transit, then, during each such focusing, the peak power density (W/cm$^2$) may increase to a value at which substantially all molecules within the appropriate ionization zone 93 (see FIG. 6B) are ionized by electron ejection. The replacement of a lens-focusing element with a mirror-focusing element, as implemented in the ion source 140 as illustrated in FIGS. 10A-10B provides for greater efficiency of light propagation, with fewer transmission losses relating to stray reflection and material absorption.

Figure 11A:
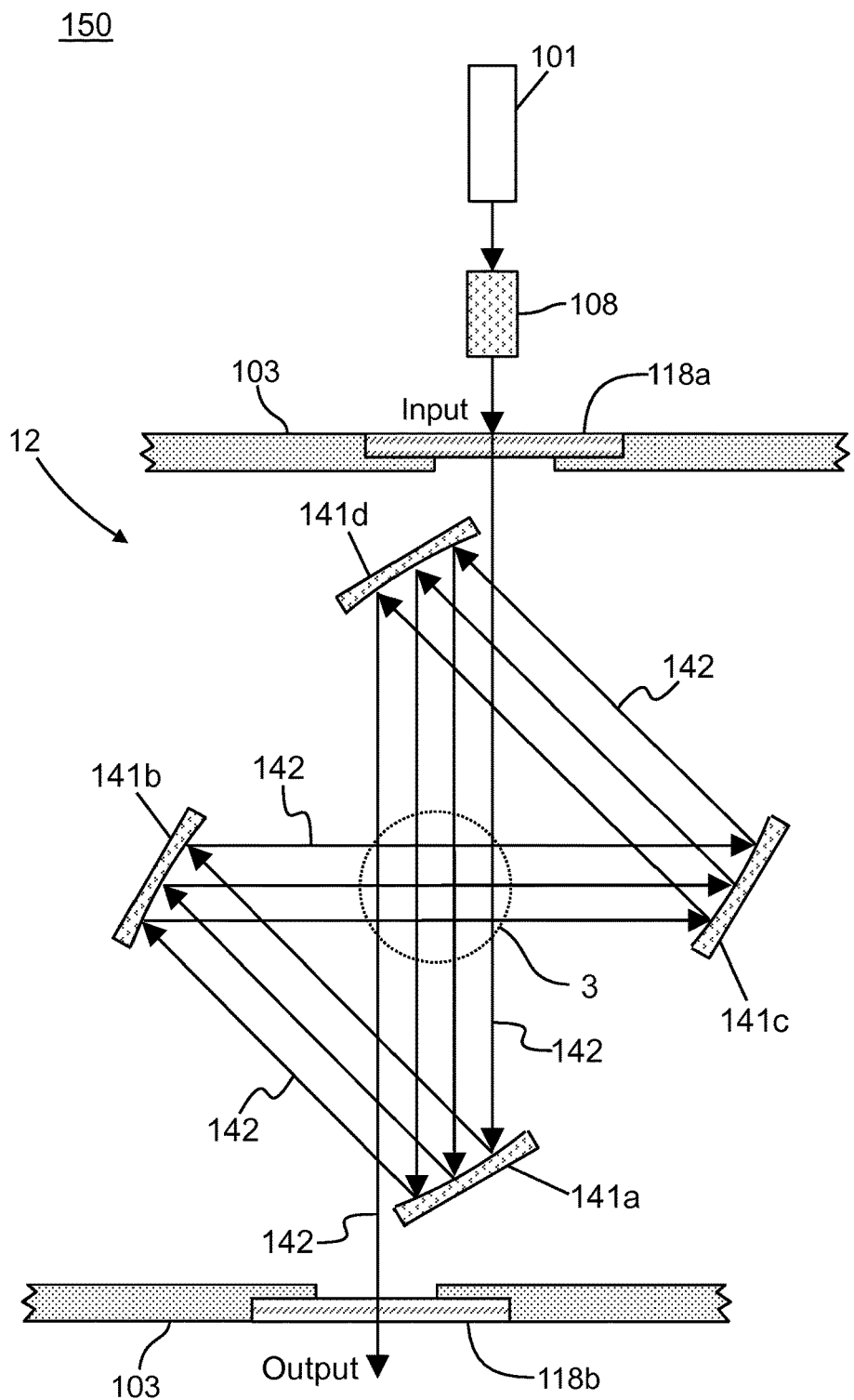
FIG. 11A is a schematic depiction of a fourth ion source for a mass spectrometer in accordance with the present teachings and comprising a bow-tie light path configuration, showing the pathway of a light pulse into the cavity at an input location and repeatedly across the effluent zone of a chromatographic column to an output location.

FIG. 11A is a schematic depiction of a fourth ion source for a mass spectrometer in accordance with the present teachings. The ion source 150 illustrated in FIG. 11A as well as in FIG. 11B comprises a bow-tie light path configuration that is enabled by a set of four turning mirrors 141a-141d as illustrated. The folded light path configuration of the ion source 150 enables a light pulse to repeatedly traverse the effluent zone of a chromatographic column 3 that is shown in end-on view in FIGS. 11A-11B and is to be understood as being disposed behind the plane of the drawings in FIGS. 11A-11B. In contrast to the closed optical cavity configurations depicted in FIGS. 8A, 8B, 9 and 10A-10B, the ion source 150 includes a folded optical path 142 between an input window 118a and an output window 118b. Because the ion source 150 does not comprise a closed optical cavity, it does not require an optical switching device or assembly (FIG. 8A-8B) within the optical path for introduction of a laser light pulse into such an optical cavity. Instead, laser pulses may be directly introduced into the ionization chamber 12 from laser 101 with only a lens or lens system 108 and the input window 118a between the laser and the ionization chamber.

In following the plurality of segments of the folded optical path 142, a light pulse from a pulsed laser 101 will repeatedly cross the effluent zone of the chromatographic column 3 within ionization chamber 12 without reversing or re-tracing its path. The so-called "walk-off" optical path configuration illustrated in FIGS. 11A-11B permits each crossing of the effluent stream by a laser pulse to interrogate a different volume element of the effluent stream. This configuration thereby avoids a potential undesirable situation in which a crossing does not induce significant additional ionization in a particular volume element of the effluent stream because all molecules in the volume element were already ionized in a prior crossing of the same pulse. For example, if analyte gas molecules are emitted from the column at the speed of sound, then a hypothetical volume element consisting of a cubic element having 10 µm sides will require about 30 ns to completely refill with fresh gas after the passage of a laser pulse through the volume element.

The turning mirrors 141a-141d preferably comprise curved reflective surfaces which can cause a light pulse to come to a focus adjacent to the outlet of column 3 within each light path segment 142 that is between the mirrors 141b and 141c and which cause collimation of the light pulse between the pair of mirrors 141a, 141b and between the pair of mirrors 141c, 141d. For example, each of the mirrors 141a-141d may be formed as an off-axis paraboloid-segment reflector, similar to the reflector 206 shown in FIG. 10B. The placement and number of such curved-surface mirrors and the exact trajectories of the light pulse segments between them may vary from those shown in FIGS. 11A-11B.

Figure 11B:
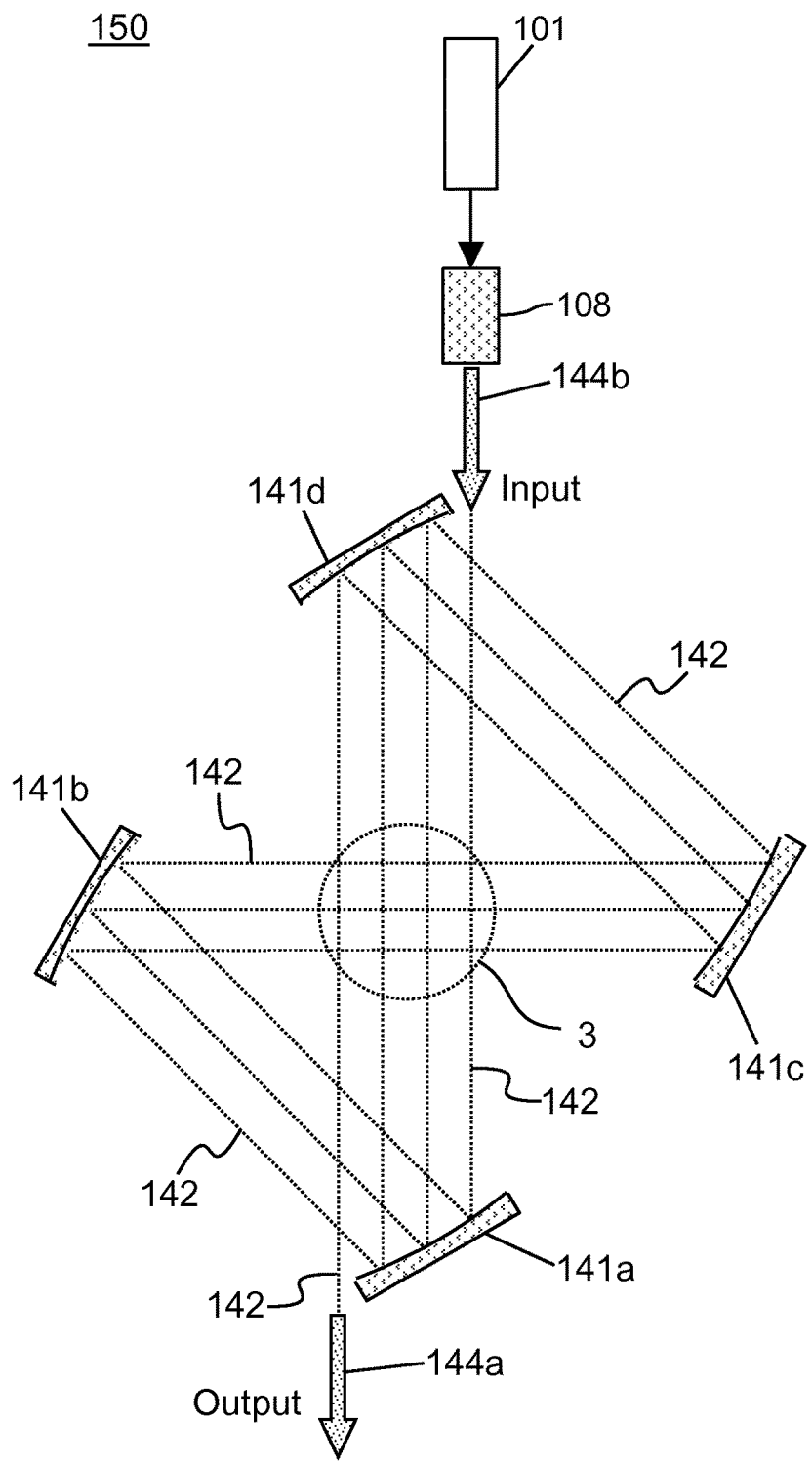
FIG. 11B is another schematic depiction of the bow-tie light path configuration of FIG. 10A, schematically showing the introduction of a second light pulse into the ionization chamber at the optical input simultaneous with the exit of a first light pulse from the ionization chamber at the optical output.

FIG. 11B is another schematic depiction of the bow-tie light path configuration of FIG. 11A, schematically showing the introduction of a second light pulse 144b into the cavity at the input simultaneous with the exit of a first light pulse 144a from the cavity at the output. For clarity, the input and output windows 118a, 118b and the ionization chamber housing are omitted from FIG. 11B. Although a total of eight crossings of the profile of the column 3 are illustrated in each of FIGS. 11A-11B, the total number of such crossings may be much greater.

Figure 12:
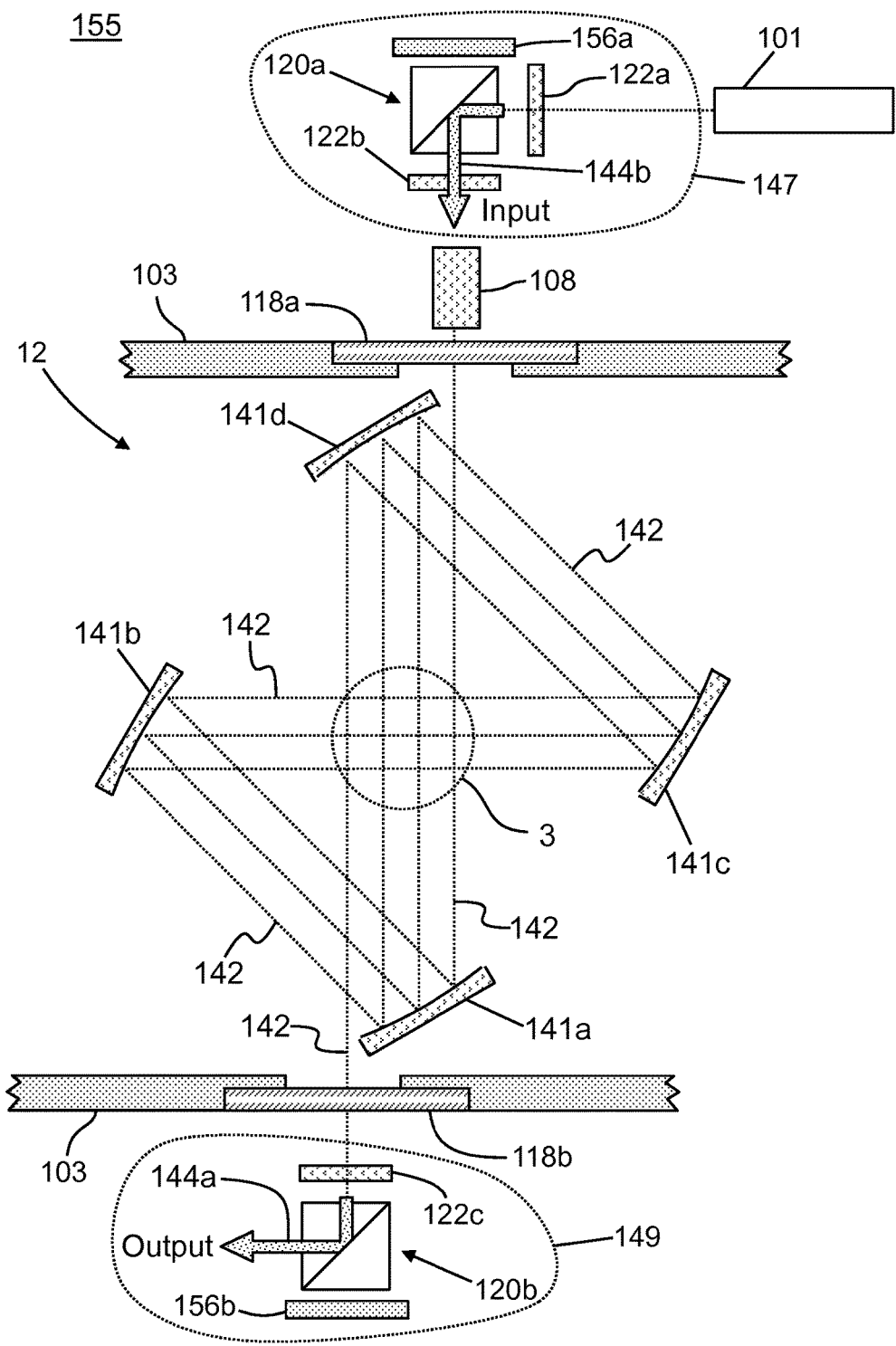
FIG. 12 is a schematic depiction of a fifth ion source for a mass spectrometer in accordance with the present teachings and comprising a bow-tie optical cavity comprising controllable beam diverting optical components at both its input and its output, schematically showing the introduction of a second light pulse into the cavity at the input simultaneous with the exit of a first light pulse from the cavity at the output.

FIG. 12 is a schematic depiction of a fifth ion source for a mass spectrometer in accordance with the present teachings. The ion source 155 depicted in FIG. 12 is a modified version of the ion source 150 illustrated in FIG. 11A. The modification includes the addition of an optical switching and reflecting assembly 147 disposed between the laser 101 and the input window 118a and another optical switching and reflecting assembly 149 disposed outside of the ionization chamber 12 down-path from the output window 118b. The illustrated optical switching and reflecting assembly 147 is similar to the optical switching device or assembly 102 illustrated in FIGS. 8A-8B and comprises a first polarization beam splitter 120a, first and second switchable polarization controlling elements 122a, 122b and first cavity mirror 156a. The other optical switching and reflecting assembly 149 includes a second polarization beam splitter 120b, a second cavity mirror 156b and another switchable polarization-controlling element 122c.

The first and second cavity mirrors 156a, 156b define the two ends of a closed optical cavity within which a light pulse may propagate both forward and backward a plurality of times along the folded light path 142. Thus, the ion source 155 illustrated in FIG. 12 combines the light path walk-off capabilities of the ion source 150 (FIGS. 11A-11B) with the closed cavity configuration of other illustrated ion source embodiments. The first polarization beam splitter 120a and first and second switchable polarization controlling elements 122a, 122b may operate similarly to the similarly numbered components in FIGS. 8A-8B. As previously described, this set of components may be operated in a first configuration (illustrated in FIG. 12) that introduces a laser light pulse 144b into the optical cavity or in an alternative configuration (not shown) that enables repeated forward and backward propagation of a light pulse along folded path 142 within the optical cavity. The second polarization beam splitter 120b and the third switchable polarization controlling elements 122c may be operated in a first configuration (illustrated in FIG. 12) that removes a laser light pulse 144a from the optical cavity or in an alternative configuration (not shown)

that enables the repeated forward and backward propagation of the light pulse between the mirrors 156a, 156b.

As schematically illustrated in FIG. 12, the operation of the components of the optical switching and reflecting assembly 147 may be synchronized with the operation of the components of the optical switching and reflecting assembly 149 such that a later light pulse 144b is introduced into the optical cavity concurrently with the removal of an earlier light pulse 144a from the optical cavity.

The set of four mirrors shown in each of FIGS. 11A, 11B and 12 may be replaced, in some embodiments, by one of numerous alternative mirror sets (not specifically illustrated) comprising other than four individual mirrors. As but one example, a set of three mirrors arranged in a triangular configuration may be employed. Preferably, however, a mirror set comprising more than four mirrors will be employed. The individual mirrors of such a set may be arranged in a configuration that surrounds the effluent that is discharged from column 3 in a roughly triangular (for exactly three mirrors), circular or elliptical surrounding configuration. The mirrors are preferably arranged such that an ionizing light pulse from a pulsed laser will reflect off each of the mirrors in a defined sequence, thereby crossing the path of the effluent multiple times and in multiple directions. At the end of the defined sequence, the light pulse may exit from an enclosing ionization chamber, as illustrated in FIG. 11A, or may be caused to repeat the reflection sequence (or a different reflection sequence) within the chamber, as in FIG. 12. Preferably, the mirrors are curved-surface mirrors arranged such that the light pulse is brought to a focused beam within the path of the effluent multiple times, thereby causing ionization at multiple points. The provision of multiple light pathways across and multiple focal points within the effluent pathway enables multiple portions of the effluent stream to be exposed to the ionizing light pulse. Such folded light pathways are beneficial because, after causing ionization of molecules at any one focal point, a light pulse may be reflected between the mirrors thousands of times before additional non-ionized molecules have an opportunity to flow into that focal point.

Figure 13A:
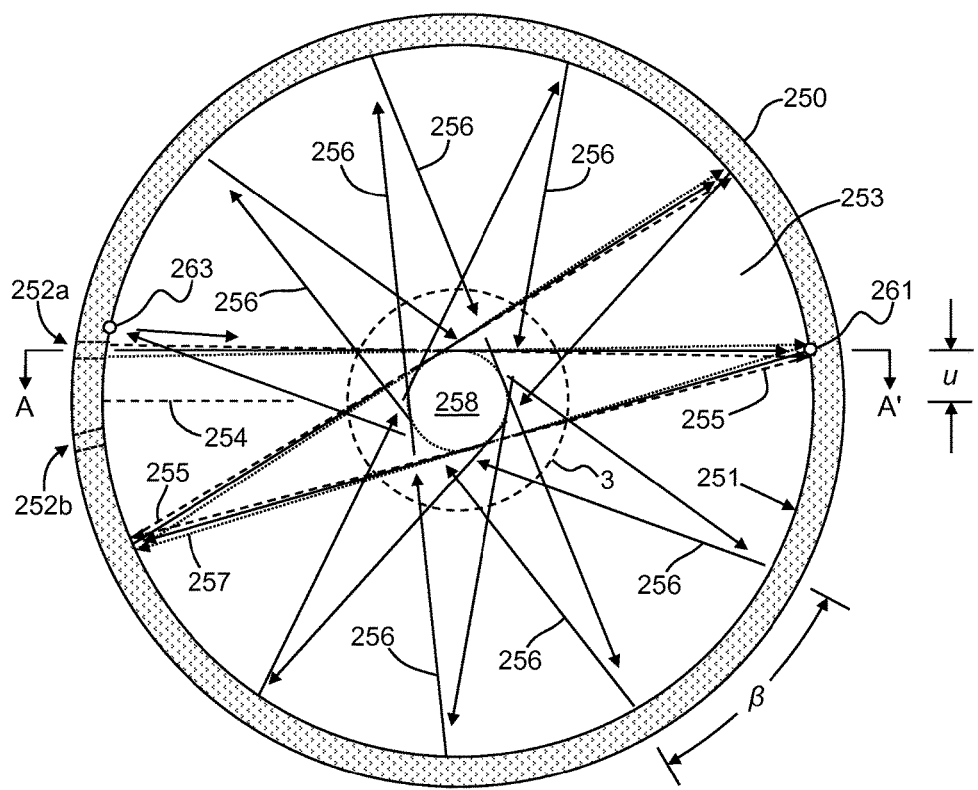
FIG. 13A is a schematic depiction of optical ray paths within the interior of a ring mirror formed as a segment of a sphere that surrounds the effluent at the end of a chromatographic column.

At the limit of an infinite number of mirrors surrounding the effluent stream within an ionization chamber, such plurality of mirrors becomes indistinguishable from a single curved mirror that forms an optical cavity surrounding the effluent that is discharged from the end of chromatographic column 3. Such a configuration is illustrated in FIG. 13A in which a single ring mirror 250 surrounds the effluent stream, thereby forming an enclosed optical cavity 253 within which each optical pulse is reflected numerous times. The ring mirror is formed as an equatorial segment of a sphere (therefore, forming a ring) as is made clear by the cross sectional view along line A-A' illustrated in FIG. 13B. The cross section A-A' is taken along a plane that includes an aperture 252a, the cross sectional plane being parallel to and offset from a diameter line 254 (i.e., a line passing through the spherical center) by a distance, u. Light pulses, comprising central ray path 256 and peripheral ray paths 255 and 257, enter the cavity 253 through aperture 252a and propagate, prior to their first reflection at mirror surface 251, within the plane of cross section A-A' and parallel to the spherical diameter line 254. Central ray path 256, of which several segments are shown in FIG. 13A illustrates the average (or general or overall) propagation path of each light pulse and peripheral ray paths 255, 257 represent the locations of the light pulse "edges" at the half-power points of each light pulse cross section. For clarity, only a few portions of the peripheral ray paths 255 and 257 are illustrated in FIG. 13A.

Prior to its entry into optical cavity 253 of mirror 250 through aperture 252a, each light pulse is caused (e.g., by optical components, not specifically shown in FIGS. 13A-13B, that are external to the mirror 250) so as to propagate within the plane of cross section A-A' parallel to the diameter line 254 and to come to an initial focus at an initial focal point 259 that is midway between the aperture 252a and a first reflection point 261 on the mirror surface 251. The initial focal point 259 is located within the plane of cross section A-A' at a distance u from the spherical center and thus defines a central spherical volume 258 of spherical radius u to which the ray path 256 is tangent at focal point 259. The initial focal point is specifically shown in FIG. 13B and is indicated in FIG. 13A by the initial crossing point of ray paths 255, 256 and 257.

After its initial reflection (at point 261), each light pulse is re-reflected off of the surface 251 numerous times within the optical cavity 253, each portion of the central ray path 256 subsequent to one of the reflections comprising a reflected segment of the light pulse pathway. As a result of the spherical geometry of the reflective surface 251 and the basic law of reflection (i.e., that the angle of incidence is equal to the angle of reflection, both angles taken with respect to a line that is normal to the tangent of the surface at the point of reflection), each reflected segment passes tangent to the surface of the internal spherical volume 258 and, furthermore, each light pulse is re-focused at each such tangent point. The first two focal points of reflected segments are indicated in FIG. 13A by the crossing points of the first two reflected portions of ray paths 255, 256 and 257. After coming to a focus on the surface (indicated by a dotted circle in FIG. 13A) of the internal spherical volume 258, the light of each pulse diverges on its continued pathway (along an individual reflected segment) back towards the reflective surface 251 at which is once again reflected so as to again focus at a different point on the surface of the internal spherical volume 258.

Successive points of light pulse reflection along the spherical equator of the reflective surface 251 alternate between approximately diametrically opposite sides of the ring mirror which progress around the spherical equator. The focal points propagate around the surface of the internal spherical volume 258 in a similar fashion. A first circuit of reflection points about the spherical equator is defined when the most recent reflection point 263 either returns to or is at or at is closest point to aperture 252a. At this point, the collection of all reflection points encountered by a light pulse during the completion of the circuit are separated by the angle $\beta$ as indicated on FIG. 13A, where $\beta$ is related to the distance u and the spherical radius R by the relation $\beta = 4 \times \tan^{-1}(u/R)$. Thus, the number of reflection points corresponding to a single circuit is determined by the radial offset (in radians) of the aperture 252a from the diameter line 254. As an additional consideration, the numerical aperture of the converging rays, as determined by external optics, and the spherical radius, R, should be chosen such that, upon re-divergence of the pulse between each focal point and a subsequent reflection point on the mirror surface, the optical power density at the reflection point is below a damage threshold of the mirror surface.

According to some embodiments in accordance with the present teachings, the physical parameter u may be chosen such that light pulses exit from the optical cavity 253 through the same aperture 252a from which they were inlet after a certain number of reflections on the spherical equator of the mirror surface 251. However, if a light pulse fails to exit the cavity at the aperture 252a, then the pulse will be re-reflected within the cavity at a different series of reflection points. For example, as illustrated in FIG. 13A, the light pulse is directed to point 263 on the mirror surface after reflecting at the series of illustrated reflection points. Since point 263 is offset from the aperture 252a, the subsequent reflected segment (shown as a short arrow) is angularly offset from the initial ray path that was followed during the inlet of the light pulse into the optical cavity. As a result, the pulse will continue to reflect off the mirror surface 251 as a subsequent set of reflection points (not illustrated) that are shifted from those shown in FIG. 13A. The pulse may thereby be temporarily trapped in the cavity so as to focus a large number of times at the surface of the inner spherical volume 258. According to alternative embodiments, a second aperture 252b may be provided within the ring mirror at a position such that light pulses exit the cavity after a certain number of reflections.

Figure 13B:
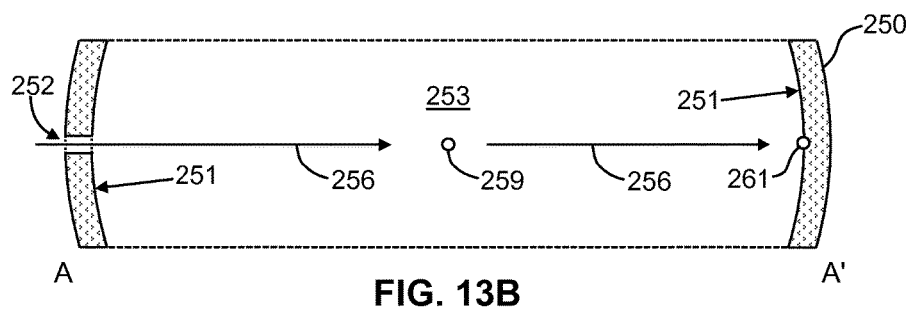
FIG. 13B is a cross sectional view through the ring mirror depicted in FIG. 13A.

According to some embodiments of ion source apparatus in accordance with the present teachings, the ring mirror 250 illustrated in FIGS. 13A-13B may replace the set of four mirrors in an ion source system configured as shown in FIG. 11A such that, upon exiting from the optical cavity 253 (such as through aperture 252b), spent light pulses exit from the ionization chamber 12. Subsequently, another pulse will be inlet to the optical cavity (for instance, through aperture 252a) after a time period determined by the pulse rate of the laser light source and further ionization of molecules in the effluent stream will be induced by the other pulse.

CONCLUSIONS

In summary, various novel ion source embodiments are disclosed that include the disposition of the exit of a chromatographic column proximal to one or more focal positions of an optical cavity for purposes of enhancing the overlap between the column effluent and laser pulse both spatially and in time. An off axis cavity comprising multiple mirrors (such as a "bow-tie" cavity comprising four mirrors) or a spherical ring mirror can be utilized to walk the beam path around the GC column effluent region. These approaches can especially enhance the efficiency of lower peak power lasers with typically high repetition rates. By moving the focus spatially around or across the effluent stream and taking advantage of the aspect ratio of the laser beam, the ionization efficiency can be improved >90%. According to some embodiments, an on axis cavity can be utilized such that pathways of laser pulses are parallel or nearly parallel to the effluent stream flow direction so as to sustain the ultra-short pulses during the pulse regeneration period. The use of such on-axis cavity configurations can especially enhance the efficiency of high peak power lasers with low repetition rates. This approach utilizes a large beam focus to reduce the effects of laser pointing stability and alignment errors and can enhance the ionization efficiency to approximately 100%. Further enhancements can be made. For example, the above two approaches may be combined, enabling the use of an extremely low average peak power laser which requires a small beam focus at low repetition rates.

Because individual laser pulses are caused to pass multiple times through the cavity, the mirrors should be chosen so as to have at least 99.99% reflectivity at the laser wavelength. Preferably, the mirror reflectivity may be 99.997% and, even more preferably, the mirror reflectivity may be 99.999%. For operational purposes, a laser pulse may be considered to be no longer advantageously useable (i.e., "spent") when the energy of the pulse drops by a factor of the square root of two (i.e., when the energy drops to about 70% of the initial energy) because it is at this energy level that ionization no longer occurs across the entire Rayleigh length surrounding a beam waist. Mirrors having 99.99% reflectivity will give rise to approximately 3500 reflections before the 70% energy threshold is crossed. Mirrors having 99.997% and 99.999% reflectivity can give rise to greater than 10000 and greater than 35000 reflections, respectively, before the 70% energy threshold is crossed.

Such numbers of passes (3000 or greater) through the effluent stream are desirable because this enables ionization to occur at a similar number (i.e., 3000 or greater) of separate and distinct volume elements during the time that any previously ionized volume element is refilling with fresh un-ionized molecules. For purposes of this discussion, a "volume element" may be considered to refer to a cylindrical region of space having a cylindrical diameter equal to the diameter of a focused beam waist and having a certain length defined relative to the Rayleigh length (e.g., see element 93 in FIG. 6B) such as, for example, twice the Rayleigh length. For a chromatograph discharging into an ionization chamber whose interior is at near-atmospheric pressure, such refill time may be on the order of one millisecond. If the column discharges into vacuum (on the order of a few millitorr or lower), the refill time may be on the order of tens of microseconds or possibly less. Assuming an optical path length of approximately 0.3 m between successive mirror reflections, then 3500 passes through an optical cavity can produce useful ionization over a time period of approximately 3500 microseconds during which time a pulse will travel over 1 km and an effluent molecule may travel 1-10 microns. Under the same assumption, 10000 passes through an optical cavity can produce useful ionization over a time period of approximately 11000 microseconds. In the most preferable embodiments of this type of system, the laser repetition rate is sufficiently great such that a subsequent pulse can be introduced into the cavity just at or after the time that the prior pulse is "spent".

Ionization in accordance with the methods and apparatuses described herein may be achieved within ionization chambers at pressures up to and above atmospheric pressure. However, depending on the requirements of particular experiments or chemical analyses, it may be advantageous to achieve ionization in accordance with the present teachings under conditions of partial vacuum or even high vacuum. For example, ionization under partial or high vacuum conditions can lead to at least the following beneficial properties: (a) more efficient separation of generated analyte ions from generated free electrons under the influence of an electric field developed in the ionization chamber; (b) faster refill of effluent molecules into a previously ionized volume element as a result of free expansion of gaseous effluent discharged into an evacuated chamber; and (c) fewer ion side reactions with background gas molecules which may complicate the more-easily-interpreted molecular ion distribution initially formed by direct strong-field laser ionization of analyte molecules. Therefore, ionization according to various embodiments may be achieved at pressures at or less than one atmosphere pressure. According to other embodiments, which may be increasingly more preferable under certain conditions or for certain analyses, ionization may be achieved at pressures at or below 10 torr, or at or below 1 torr, or at or below 500 millitorr, or at or below 1 millitorr ($10^{-3}$ torr), at or below 0.1 millitorr ($10^{-4}$ torr) or at or below 0.01 millitorr ($10^{-5}$ torr).

All patents, patent application publications and technical publications mentioned herein are hereby incorporated herein by reference in their entirety except that, insofar as any such patent or publication contradicts the present disclosure, then the present disclosure shall control.

What is claimed is:

1. An ion source for a mass spectrometer for ionizing a gaseous sample effluent stream, comprising:
    an evacuated chamber having an interior receiving the gaseous sample effluent stream from an outlet end of a gas chromatograph (GC) column;
    a source of light pulses of pulse width 150 femtoseconds (fs) or less;
    a window of the evacuated chamber through which the light pulses pass into the evacuated chamber interior;
    one or more mirrors within the evacuated chamber disposed such that the light pulses are reflected from each of the one or more mirrors such that the reflected pulses are caused to focus at one or more focal regions within the effluent stream within the evacuated chamber interior; and
    a pair of electrodes disposed at opposite sides of the one or more focal regions,
    wherein a first one of the one or more mirrors comprises a concave reflective surface that is a segment of a sphere and wherein the GC column passes through an aperture within the first one of the one or more mirrors.

2. An ion source as recited in claim 1, wherein the GC column outlet end is recessed away within the reflective surface and within the first one of the one or more mirrors.

3. An ion source as recited in claim 1, further comprising a voltage source electrically coupled to the two electrodes and configured to apply a negative bias voltage to a one of the electrodes disposed between the one or more focal regions and an inlet aperture of an evacuated chamber of the mass spectrometer.

4. A method of ionizing a sample for mass analysis by a mass spectrometer, comprising:
    introducing a gaseous effluent stream of the sample into an interior of an evacuated chamber;
    causing a plurality of light pulses to be focused within a path of the effluent stream within the evacuated chamber interior, wherein each light pulse is caused to be focused within the path of the effluent stream a plurality of times such that positive ions of the sample are generated during each focusing; and
    causing at least a portion of the positive ions to migrate towards and into an inlet aperture of the mass spectrometer,
    wherein the causing of each light pulse to be focused within the path of the gaseous effluent stream a plurality of times comprises causing each light pulse to be reflected at each of a plurality of mirrors disposed within the evacuated chamber interior, and
    wherein the introducing of the gaseous effluent stream of the sample into the interior of the evacuated chamber comprises introducing the gaseous effluent stream of the sample into the evacuated chamber interior from an outlet end of a gas chromatograph (GC) column that is disposed within an aperture of a one of the plurality of mirrors.

5. A method of ionizing a sample as recited in claim 4, wherein the introducing of the gaseous effluent stream of the sample into the interior of the evacuated chamber comprises introducing the gaseous effluent stream of the sample into the evacuated chamber interior maintained at a pressure of $10^{-5}$ Torr or less.

6. A method of ionizing a sample as recited in claim 4, wherein the causing of the at least a portion of the positive ions to migrate towards and into an inlet aperture of the mass spectrometer includes causing free electrons that are generated during the generation of the positive ions to be separated from the positive ions under the influence of an electric field applied by electrodes disposed at opposite sides of each focused light pulse.

7. A method of ionizing a sample for mass analysis by a mass spectrometer, comprising:
    introducing a gaseous effluent stream of the sample into an interior of an evacuated chamber;
    causing a plurality of light pulses to be focused within a path of the effluent stream within the evacuated chamber interior, wherein each light pulse is caused to be focused within the path of the effluent stream a plurality of times such that positive ions of the sample are generated during each focusing; and
    causing at least a portion of the positive ions to migrate towards and into an inlet aperture of the mass spectrometer,
    wherein the causing of each light pulse to be focused within the path of the gaseous effluent stream a plurality of times comprises causing each light pulse to be focused at least one time by a lens and at least one time by a mirror having a concave reflective surface that is a segment of a sphere, wherein each focusing is between the lens and the mirror, and
    wherein the introducing of the gaseous effluent stream of the sample into the interior of the evacuated chamber comprises introducing the gaseous effluent stream of the sample into the evacuated chamber interior from an outlet end of a gas chromatograph (GC) column that is disposed within an aperture of the mirror.

8. A method of ionizing a sample as recited in claim 7, wherein the introducing of the gaseous effluent stream of the sample into the interior of the evacuated chamber comprises introducing the gaseous effluent stream of the sample into the evacuated chamber interior maintained at a pressure of $10^{-5}$ Torr or less.

9. A method of ionizing a sample as recited in claim 7, wherein the causing of the at least a portion of the positive ions to migrate towards and into an inlet aperture of the mass spectrometer includes causing free electrons that are generated during the generation of the positive ions to be separated from the positive ions under the influence of an electric field applied by electrodes disposed at opposite sides of each focused light pulse.

* * * * *